United States Patent
Li

(10) Patent No.: US 10,718,755 B2
(45) Date of Patent: Jul. 21, 2020

(54) METHOD FOR SCREENING PHARMACEUTICALS FOR TREATMENT OF STEATOHEPATITIS USING N-TERMINAL DIMERIZATION OF APOPTOSIS SIGNAL-REGULATED KINASE1

(71) Applicant: WUHAN UNIVERSITY, Wuhan (CN)

(72) Inventor: Hongliang Li, Wuhan (CN)

(73) Assignee: WUHAN UNIVERSITY, Wuhan (CN)

( * ) Notice: Subject to any disclaimer, the term of this patent is extended or adjusted under 35 U.S.C. 154(b) by 154 days.

(21) Appl. No.: 15/821,865

(22) Filed: Nov. 24, 2017

(65) Prior Publication Data

US 2018/0149638 A1    May 31, 2018

(30) Foreign Application Priority Data

Nov. 25, 2016  (CN) .......................... 2016 1 1054148
Nov. 25, 2016  (CN) .......................... 2016 1 1054149

(51) Int. Cl.

| | |
|---|---|
| *G01N 33/567* | (2006.01) |
| *G01N 33/50* | (2006.01) |
| *C12Q 1/48* | (2006.01) |
| *C12N 9/12* | (2006.01) |
| *C07K 14/00* | (2006.01) |
| *C12N 5/071* | (2010.01) |

(52) U.S. Cl.

CPC ....... *G01N 33/5044* (2013.01); *C07K 14/001* (2013.01); *C12N 5/0686* (2013.01); *C12N 9/1205* (2013.01); *C12Q 1/485* (2013.01); *C12Y 207/11025* (2013.01); *G01N 33/502* (2013.01); *C07K 2319/41* (2013.01); *C07K 2319/42* (2013.01); *C12N 2510/00* (2013.01); *G01N 2333/912* (2013.01); *G01N 2500/04* (2013.01); *G01N 2800/085* (2013.01)

(58) Field of Classification Search

CPC .................................................. G01N 33/5044
See application file for complete search history.

(56) References Cited

U.S. PATENT DOCUMENTS

| | | | |
|---|---|---|---|
| 2006/0035823 A1* | 2/2006 | Lederman .............. | C07K 14/47 424/278.1 |
| 2006/0094059 A1* | 5/2006 | Westwick .......... | G01N 33/5005 435/7.1 |
| 2010/0137144 A1* | 6/2010 | Remacle ................ | C12Q 1/485 506/7 |
| 2014/0200261 A1* | 7/2014 | Hoge .................. | A61K 31/7105 514/44 R |
| 2014/0315214 A1* | 10/2014 | Taipale ............ | G01N 33/54306 435/7.4 |
| 2015/0182581 A1* | 7/2015 | Tripathi ............... | C07K 14/005 514/3.8 |

OTHER PUBLICATIONS

Purbey et al (NAR , 2008, vol. 36, No. 7, pp. 2107-2122, published online Jan. 10, 2008), (Year: 2008).*
Score report for SEQ ID No. 1 & 2 per Hoge et (Year: 2014).*

* cited by examiner

*Primary Examiner* — Catherine S Hibbert
(74) *Attorney, Agent, or Firm* — Matthias Scholl P.C.; Matthias Scholl

(57) ABSTRACT

A method for screening a pharmaceutical compound for prevention, alleviation and/or treatment of steatohepatitis, the method including employing N-terminal dimerization of an apoptosis signal-regulated kinase 1 as a target.

7 Claims, 15 Drawing Sheets

Specification includes a Sequence Listing.

METHOD FOR SCREENING PHARMACEUTICALS FOR TREATMENT OF STEATOHEPATITIS USING N-TERMINAL DIMERIZATION OF APOPTOSIS SIGNAL-REGULATED KINASE1

CROSS-REFERENCE TO RELATED APPLICATIONS

Pursuant to 35 U.S.C. § 119 and the Paris Convention Treaty, this application claims foreign priority to Chinese Patent Application No. 201611054148.9 filed Nov. 25, 2016, and to Chinese Patent Application No. 201611054149.3 filed Nov. 25, 2016. The contents of all of the aforementioned applications, including any intervening amendments thereto, are incorporated herein by reference.

BACKGROUND OF THE INVENTION

Field of the Invention

The present disclosure relates to the construction of a screening model using N-terminal dimerization of apoptosis signal-regulated kinase 1 (ASK1) as a target and using of a screened ASK1 N-terminal dimerization inhibitor in preparation of a pharmaceutical compound for prevention, alleviation and/or treatment of steatohepatitis.

Description of the Related Art

Apoptosis signal-regulated kinase 1 (ASK1) is a member of the mitogen-activated protein kinase (MAPKKK) family. ASK1 has an important regulatory role for a variety of diseases, which can promote Ang II-induced cardiac hypertrophy, cardiac remodeling, interstitial fibrosis and coronary artery remodeling, etc., and can promote the death of neurons-microglial cells after cerebral ischemia reperfusion, thus worsening the development of stroke disease.

ASK1 is significantly activated in the model of acute renal injury induced by ischemia reperfusion. Based on the ASK1 activation mechanism and its regulation of a variety of diseases, studies have been conducted to develop pharmaceuticals that can regulate the signal cascade of ASK1.

The liver is a major regulator of carbohydrate metabolism and lipid metabolism in the body, nonalcoholic steatohepatitis (NASH) is a disease characterized by hepatocyte lipid aggregation, hepatic steatosis, and inflammatory response. Currently, the treatment is mainly focused on disease complications, such as insulin resistance, hyperglycemia, obesity; the therapeutic effect is very limited. Therefore, how to effectively treat steatohepatitis and how to effectively screen for pharmaceuticals that can effectively treat steatohepatitis are problems that need to be urgently solved at this stage.

SUMMARY OF THE INVENTION

In view of the above-described problems, it is one objective of the invention to provide a use of apoptosis signal-regulated kinase 1 for screening a pharmaceutical compound for treatment of steatohepatitis using N-terminal dimerization of apoptosis signal-regulated kinase 1 as a target, where the pharmaceutical compound can inhibit the N-terminal dimerization of the apoptosis signal-regulated kinase 1.

"N-terminal dimerization" of the apoptosis signal-regulated kinase 1 (ASK1) refers to two ASK1 monomers binding to each other through a coiled helix domain located at its N-terminal to form a dimeric polymer. Specifically, under normal conditions, ASK1 binds to each other through its C-terminal crimped helix domains to form homodimers. In this case, internal small molecule Trx binds to the N terminal of ASK1, blocks the N-terminal polymerization of ASK1 and inhibits the activation of ASK1. While in the stimulation of factors such as active oxygen, Trx undergoes an oxidation reaction and then dissociates from ASK1, causing the ASK1 N-terminal to form a dimeric polymer, resulting in activation of ASK1.

Steatohepatitis is a liver disease that is secondary to the inflammation and fibrosis in liver steatosis and cell damage, and is divided into nonalcoholic steatohepatitis and alcoholic steatohepatitis by its cause. In the present disclosure, steatohepatitis mainly refers to non-alcoholic steatohepatitis, and its liver histopathological changes are similar to alcoholic steatohepatitis, but the patient has no clear drinking history. Nonalcoholic steatohepatitis will further develop into cirrhosis, hepatocellular carcinoma and liver failure.

In a second aspect of the present disclosure, a method for screening a pharmaceutical compound for prevention, alleviation and/or treatment of steatohepatitis using N-terminal dimerization of apoptosis signal-regulated kinase 1 as a target is provided, the method comprising the following steps:

(a) contacting a system containing an N terminal of the apoptosis signal-regulated kinase 1 and a candidate substance, wherein the system containing the N terminal of the apoptosis signal-regulated kinase 1 is a cell comprising the N terminal of the apoptosis signal-regulated kinase 1 or a solution containing the N terminal of the apoptosis signal-regulated kinase 1; and (b) observing the effect of the candidate substance on the N-terminal dimerization of the apoptosis signal-regulated kinase 1;

wherein the candidate substance is a potential substance for prevention, alleviation and/or treatment of steatohepatitis when the candidate substance can inhibit the N-terminal dimerization of the apoptotic signal-regulated kinase 1.

In a class of this embodiment, step (a) comprises: adding the candidate substance to the system containing the N terminal of the apoptosis signal-regulated kinase 1 in a test group; and/or step (b) comprises: detecting the role of the N-terminal dimerization of the apoptosis signal-regulated kinase 1 in the system in the test group and comparing with a control group, wherein the control group is a system containing N-terminal dimerization of an apoptosis signal-regulated kinase 1 without addition of the candidate substance; wherein the candidate substance is a potential substance for prevention, alleviation and/or treatment of steatohepatitis when the test result in the test group indicates that the N-terminal dimerization of the apoptosis signal-regulated kinase 1 is inhibited.

In a class of this embodiment, step (a) comprises:

(1) selecting a CheckMate™ mammalian two-hybrid system for use, connecting the DNA fragment encoding the N-terminal 1-678 aa of the apoptotic signal-regulated kinase 1 to the pBIND vector encoding the DNA binding domain and the pACT vector encoding the transcriptional activation domain respectively, and then transfecting the two constructed vectors into an animal cell to construct an apoptotic signal-regulated kinase 1 N-terminal dimerization mammalian two-hybrid screening system;

wherein an amino acid sequence encoding the N-terminal (amino acids from 1 to 678) of the apoptosis signal-regulated kinase 1 is shown in SEQ. ID. NO: 1 and the DNA sequence is shown in SEQ. ID. NO: 2;

(2) connecting nucleotide fragments of a candidate polypeptide to a psi-Flag vector, respectively, and simultaneously transfecting candidate polypeptide plasmids psi-flag-Peptides and pG5luc into the above constructed animal cell for screening the N-terminal dimerization of apoptosis signal-regulated kinase 1;

step (b) comprises: detecting RLUs of firefly luciferase and *Renilla* luciferase after 24 hrs of incubation of a successfully transfected cell and calculating a ratio of the two, and comparing degrees of inhibition of the polypeptides from different samples according to an obtained ratio.

If the N terminal of the apoptosis signal-regulated kinase 1 is normally dimerized, the firefly luciferase reporter gene is highly expressed when the above cells continue to be transfected with the pG5luc vector, when the N-terminal dimerization of the apoptotic signal-regulated kinase 1 is inhibited, the firefly luciferase reporter gene on the pG5luc vector is not expressed. The N-terminal dimerization of the apoptotic signal-regulated kinase 1 can be analyzed by the dual-Luciferase dual luciferase reporter assay system;

wherein the transfection refers to a process of transferring or transporting a nucleic acid having a biological function into a cell and maintaining the biological functions of nucleic acids in the cell. In the embodiments of this patent, a biologically functionalized nucleic acid refers to a pBIND vector connected with DNA fragment encoding the N-terminal of aa 1 to 678 of the apoptotic signal-regulated kinase 1, a pACT vector connected with DNA fragment encoding the N-terminal of aa 1 to 678 of the apoptotic signal-regulated kinase 1, a pG5luc vector, a plasmid pcDNA5-HA, a plasmid pcDNA5-Myc, a plasmid HA-ASK1$_N$, a plasmid Myc-ASK1$_N$, or a psi-Flag plasmid to which a candidate polypeptide nucleotide fragment is connected. In another preferred embodiment, the animal cell used in step (a) of the screening method is selected from HEK-293T, L02, Hela, Huh7, Hepg2, A549, 3T3, MEFs, and H9C2.

HEK-293T, human embryonic kidney cell, purchased from Cell bank of Chinese Academy of Sciences, catalog number GNHu43.

L02, human liver cell line, purchased from Cell bank of Chinese Academy of Sciences, catalog number GNHu6.

Hela, human cervical cancer cell, purchased from Cell bank of Chinese Academy of Sciences, catalog number TCHu187. Keratin immunoperoxidase staining is positive. Has been detected by mycoplasma, STR detection.

Huh7, human hepatocarcinoma cell, purchased from Cell bank of Chinese Academy of Sciences, catalog number TCHu182.

Hepg2, human hepatocellular carcinoma, purchased from Cell bank of Chinese Academy of Sciences, catalog number TCHu72.

A549, human non-small cell lung cancer cell, purchased from Cell bank of Chinese Academy of Sciences, catalog number TCHu150.

3T3, mouse embryo cell, purchased from Cell bank of Chinese Academy of Sciences, catalog number GNM6.

MEFs, mouse embryonic fibroblasts, purchased from Cell bank of Chinese Academy of Sciences, catalog number SCSP-101.

H9C2, rat cardiomyocytes, purchased from Cell bank of Chinese Academy of Sciences, catalog number GNRS. Clonal cell strains of BD1X rat embryonic heart tissue has been subcloned H9c2(2-1) cell strain.

In another preferred embodiment, the animal cell used in step (a) of the screening method is selected from HEK-293T.

In a third aspect of the present disclosure, a cell model for screening a pharmaceutical compound for prevention, alleviation and/or treatment of steatohepatitis using the N-terminal dimerization of apoptosis signal-regulated kinase 1 as a target is provided, wherein a CheckMate™ mammalian two-hybrid system is used, the DNA (SEQ. ID. NO: 2) encoding the N-terminal 1-678 aa of the apoptotic signal-regulated kinase 1 is connected to the pBIND vector encoding the DNA binding domain and the pACT vector encoding transcriptional activation domain. The two constructed vectors are transfected into an animal cell to construct a cell model for screening a pharmaceutical compound for prevention, alleviation and/or treatment of steatohepatitis. The animal cell used is selected from HEK-293T, L02, Hela, Huh7, Hepg2, A549, 3T3, MEFs, and H9C2.

In a class of this embodiment, step (a) comprises:

(1) connecting the DNA fragment encoding the N-terminal of aa 1 to 678 of the apoptosis signal-regulated kinase 1 to plasmids pcDNA5-HA and pcDNA5-Myc, respectively, constructing plasmids HA-ASK1$_N$ and Myc-ASK1$_N$, and transfecting into an animal cell respectively or simultaneously;

(2) connecting the DNA of encoding the candidate polypeptide to the psi-Flag vector, respectively, and transfecting the constructed plasmid psi-flag-Peptides into an animal cell containing both plasmids HA-ASK1$_N$ and Myc-ASK1$_N$ respectively;

step (b) comprises: detecting the contents of HA-ASK1$_N$ and Myc-ASK1$_N$ by co-immunoprecipitation and Western blot after 24 hrs of incubation of a successfully transfected cell;

wherein co-immunoprecipitation refers to a method developed using the specific binding of antigen proteins and antibodies and the phenomenon of bacterial protein "protein A/G" specifically binding to the FC fragment of antibodies (immunoglobulins). At present, it is common to pre-combine protein A/G with agarose beads so that after its reaction with the solution containing antigen and antibodies, the protein A/G on the beads can achieve the purpose of adsorption of the antigen. The antigen of interest can be separated from the other antigens from a solution containing the antigen of interest by low-speed centrifugation.

In the embodiment of the present patent, the antibody is HA antibody (anti-HA), and the antigen of interest is HA. The solution containing antigen refers to the supernatant of HEK-293T cell lysate transfected respectively with HA-ASK1$_N$, Myc-ASK1$_N$, HA-ASK1$_N$+Myc-ASK1$_N$, HA-ASK1$_N$+Myc-ASK1$_N$+psi-flag-Peptide1, HA-ASK1$_N$+Myc-ASK1$_N$+psi-flag-Peptide2, HA-ASK1$_N$+Myc-ASK1$_N$+psi-flag-Peptide3 or HA-ASK1$_N$+Myc-ASK1$_N$+psi-flag-Peptide4 and cultured for 24 hrs. Anti-HA connects the antigen of interest to protein A/G agarose beads.

Western blot uses anti-Myc as primary antibody, when an animal cell group transfected with HA-ASK1$_N$, Myc-ASK1$_N$ and candidate psi-flag-Peptide is identical to a control group transfected with HA-ASK1$_N$ or Myc-ASK1$_N$ alone, no significant Myc protein bands are detected, the candidate substance is a potential substance for prevention, alleviation and/or treatment of steatohepatitis.

In another preferred embodiment, the animal cell used in step (a) of the above-described screening method is selected from HEK-293T, L02, Hela, Huh7, Hepg2, A549, 3T3, MEFs, and H9C2.

In another preferred embodiment, the animal cell used in the above-described screening method is selected from HEK-293T.

In a fourth aspect of the present disclosure, a cell model for screening a pharmaceutical compound for prevention, alleviation and/or treatment of steatohepatitis using the N-terminal dimerization of apoptosis signal-regulated kinase 1 as a target is provided, wherein the DNA (SEQ. ID. NO: 2) fragment encoding the N-terminal 1-678 amino acids of the apoptosis signal-regulated kinase 1 is connected to plasmids pcDNA5-HA and pcDNA5-Myc, respectively, plasmids HA-ASK1$_N$ and Myc-ASK1$_N$ are constructed. The constructed plasmids are transfected into an animal cell respectively or simultaneously, and the animal cell used is selected from HEK-293T, L02, Hela, Huh7, Hepg2, A549, 3T3, MEFs, and H9C2. In another preferred embodiment, a further cellular and/or animal test is performed on the obtained potential substance to select a substance that inhibits the N-terminal dimerization of apoptosis signal-regulated kinase 1 for prevention, alleviation and/or treatment of steatohepatitis.

In a fifth aspect of the present disclosure, a polypeptide Peptide1 for prevention, alleviation and/or treatment of steatohepatitis screened using the N-terminal dimerization of apoptosis signal-regulated kinase 1 as a target is provided, wherein an amino acid sequence thereof is shown in SEQ. ID. NO: 20, or a pharmaceutically-acceptable salt thereof.

In a sixth aspect of the present disclosure, a polynucleotide molecule is provided, wherein the polynucleotide molecule encodes the polypeptide Peptide1, and the nucleotide sequence thereof is shown in SEQ. ID. NO: 24.

In a seventh aspect of the present disclosure, a pharmaceutical composition is provided, comprising:
(a) the above mentioned polypeptide Peptide1 or a pharmaceutically-acceptable salt thereof; and
(b) a pharmaceutically-acceptable carrier or excipient.

The present disclosure utilizes the liver-targeted gene therapy vector of adeno-associated virus AAV8 to mediate the overexpression of screened polypeptide Peptide1 in liver tissue of cynomolgus monkeys (Macaca. fascicularis). Through the study on the function of Peptide1 by diet induced obesity (DIO), it is found that there is no significant difference in weight and BMI index of monkey between AAV8-GFP-Peptide1 group and AAV8-GFP control group. The result of the determination of blood lipid and enzyme (ALT, AST) activity that reflects liver function shows that the contents of triglyceride and low density cholesterol and ALT enzyme activity are significantly decreased, and the content of high density cholesterol is increased in the serum of AAV8-GFP-Peptide1 group; the result of liver histopathological staining shows that lipid accumulation is significantly reduced and hepatic steatosis is significantly mitigated in the liver of monkeys of AAV8-GFP-Peptide1 group. This indicates that the polypeptide Peptide1 can inhibit the development of steatohepatitis in cynomolgus monkeys.

In an eighth aspect of the present disclosure, a method for modulating hepatic steatosis is provided, comprising: regulating N-terminal dimerization of intracellular apoptosis signal-regulated kinase 1.

The main advantages of the present disclosure are:
through the study of the mechanism of ASK1 in the high-fat diet-induced hepatic steatosis model of the present disclosure, it is firstly found that the N-terminal dimerization of ASK1 has an important regulatory effect on hepatocyte steatosis and can promote the development of hepatic steatosis. A novel pharmaceutical compound for prevention, alleviation and/or treatment of steatohepatitis can be screened using N-terminal dimerization of ASK1 as a target and by detecting whether the candidate substance can inhibit the N-terminal dimerization of ASK1.

BRIEF DESCRIPTION OF THE DRAWINGS

FIGS. 4A-4B are detection results of oil red O staining and quantitative determination result of intracellular triglyceride content in L02 cells which have been transfected with different polypeptide plasmids after stimulation with PA for 12 h, wherein FIG. 4A is the oil red O staining and FIG. 4B is a statistical chart of the detection result of triglyceride content;

FIGS. 5A-5B are detection results of Peptide1 overexpression efficiency of cynomolgus monkeys' liver mediated by adeno-associated virus AAV8, wherein FIG. 5A is a result of virus transfection efficiency of cynomolgus monkeys' liver in saline control group, AAV8-GFP control group and AAV8-GFP-Peptide1 group; FIG. 5B is a detection result of Peptide1 expression of cynomolgus monkeys' liver in AAV8-GFP control group and AAV8-GFP-Peptide1 group after portal vein injection of viral vectors;

FIGS. 6A-6B illustrate a weight and BMI index result of cynomolgus monkeys in AAV8-GFP and AAV8-GFP-Peptide1 group, wherein FIG. 6A is a graph showing the weight result, FIG. 6B is a graph showing the BMI index result (n. s.: p>0.05 vs AAV8-GFP group);

FIGS. 7A-7F illustrate blood lipid levels and a liver function detection result of cynomolgus monkeys in AAV8-GFP and AAV8-GFP-Peptide1 group, wherein FIG. 7A is a graph showing a detection result of serum triglyceride content, FIG. 7B is a graph showing a detection result of total cholesterol content, FIG. 7C is a graph showing a detection result of serum high-density cholesterol content, FIG. 7D a graph showing is a detection result of serum low-density cholesterol content, FIG. 7E is a graph showing a detection result of alanine aminotransferase (ALT) content, and FIG. 7F is a graph showing a detection result of aspartate transaminase (AST) content (n. s. p>0.05 vs AAV8-GFP group, **: p<0.01 vs AAV8-GFP group)

DETAILED DESCRIPTION OF THE EMBODIMENTS

Figure 1:
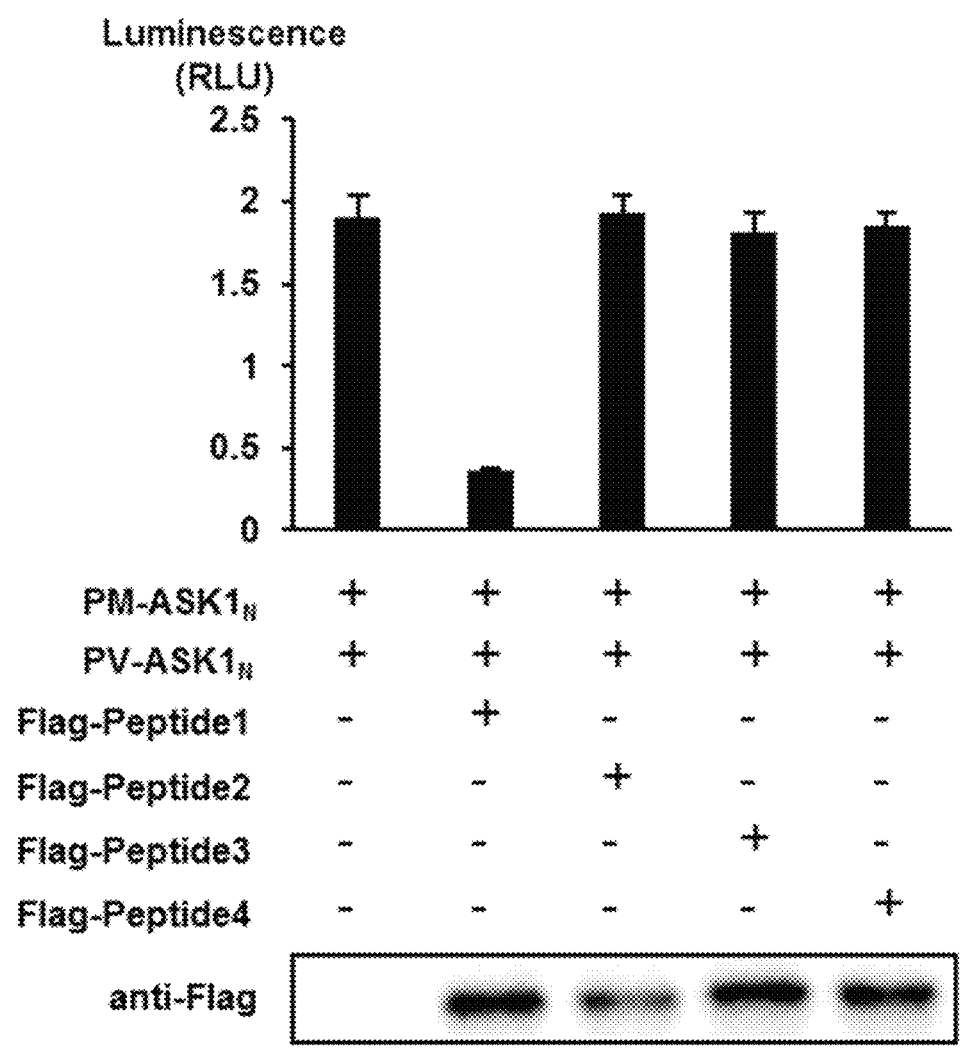
FIG. 1 is a ratio of RLUs of firefly luciferase and Renilla luciferase.

The features and advantages of the present disclosure can be further understood from the following detailed description in conjunction with the accompanying drawings. The embodiments provided are merely illustrative of the method of the present disclosure and are not intended to limit the remainder of the present disclosure in any way.

Methods:
(1) Cell Culture
HEK-293T cells are cultured in DMEM high glucose medium (containing 10% FBS, 1% penicillin-streptomycin); L02 cells are cultured in DMEM high glucose medium (containing 10% FBS, 1% penicillin—streptomycin), the air humidity in the incubator should be ensured, the CO2 content is 5% and the incubation temperature is 37° C.

(2) Vector Construction

1) Construction of Mammalian Two-Hybrid Detection Vectors pACT-ASK1$_N$ and pBIND-ASK1$_N$ Construction of ASK1$_N$ dimerization detection vector selecting a CheckMate™ mammalian two-hybrid system (Promega, E2440):

i) The ASK1(NCBI: BC088829) cDNA is used as template to amplify the ASK1$_{N1}$ fragment, the primer pairs are as follows:

```
Forward:
                                    (SEQ. ID. NO: 3)
5'-CGGGATCCGGATGAGCACGGAGGCGGACGA-3'

Reverse:
                                    (SEQ. ID. NO: 4)
5'-TGATGTCATTCTGGTGCTCCTCGCCCTCGC-3';
``` ii) The ASK1 (NCBI: BC088829) cDNA is used as template to amplify the ASK1$_{N2}$ fragment, the primer pairs are as follows:

```
Forward:
                                    (SEQ. ID. NO: 5)
5'-GGAGCACCAGAATGACATCAGGAAAGCTCG-3

Reverse:
                                    (SEQ. ID. NO: 6)
5'-GCTCTAGATCAATCATATTCATAGTCATACTCCAGC-3'
``` iii) The ASK1$_{N1}$ and ASK1$_{N2}$ mixture is used as template to amplify ASK1$_N$ fragment, the primer pairs are as follows:

```
Forward:
                                    (SEQ. ID. NO: 3)
5'-CGGGATCCGGATGAGCACGGAGGCGGACGA-3

Reverse:
                                    (SEQ. ID. NO: 6)
5'-GCTCTAGATCAATCATATTCATAGTCATACTCCAGC-3'
``` iv) pACT vector and pBIND vector are digested with BamH I (NEB, R0136L) and Xba I (NEB, R0145L) and then connected with the amplified target gene to obtain pACT-ASK1$_N$ and pBIND-ASK1$_N$ vectors.

2) Construction of pcDNA5-HA, pcDNA5-Myc, psi-Flag Vectors

Construction of pcDNA5-HA:

i) Two complementary fragments containing an HA tag sequence are synthesized:

```
                                    (SEQ. ID. NO: 9)
F-
AGCTTGCCACCATGTACCCATACGATGTTCCAGATTACGCTAGCCCGGG
G (SEQ. ID. NO: 10)
R-
GATCCGCCCGGGCTAGCGTAATCTGGAACATCGTATGGGTACATGGTGGC
A
``` ii) Two fragments are annealed to obtain a product with a cohesive end;

iii) The pcDNA™5/FRT mammalian expression vector (Thermo, V601020) is linearized with the following primers and digested with HindIII (NEB, R0104L) and BamH I;

```
pcDNA5-VF:
                                    (SEQ. ID. NO: 11)
CGCGGATCCACTAGTCCAGTGTGGTGGAA pcDNA5-VR:
                                    (SEQ. ID. NO: 12)
CCCAAGCTTAAGTTTAAACGCTAGAGTCCGGA
``` iv) The annealed product is connected with the digested linearized vector to obtain the pcDNA5-HA vector.

Construction of pcDNA5-Myc:

i) Two complementary fragments containing a Myc tag sequence are synthesized:

```
                                    (SEQ. ID. NO: 13)
F-
AGCTTGCCACCATGGAGCAGAAGCTGATCTCAGAGGAGGACCTGAGCCCGG
GCG (SEQ. ID. NO: 14)
R-
GATCCGCCCGGGCTCAGGTCCTCCTCTGAGATCAGCTTCTGCTCCATGG
TGGCA
``` ii) Two fragments are annealed to obtain a product with a cohesive end;

iii) The pcDNA™5/FRT mammalian expression vector (Thermo, V601020) is linearized with the following primers and digested with HindIII and BamH I;

```
pcDNA5-VF:
                                    (SEQ. ID. NO: 11)
CGCGGATCCACTAGTCCAGTGTGGTGGAA pcDNA5-VR:
                                    (SEQ. ID. NO: 12)
CCCAAGCTTAAGTTTAAACGCTAGAGTCCGGA
``` iv) The annealed product is connected with the digested linearized vector to obtain the pcDNA5-Myc vector.

Construction of psi-Flag:

the following fragment is synthesized:

```
                                    (SEQ. ID. NO: 15)
5'-
CCGGCTAGCGATTACGCCAAGCTCGAAATTAACCCTCACTAAAGGGAACA

AAAGCTGGAGCTCCACCGCGGTGGCGGCCGCCACCATGGATTACAAGGAT

GACGACGATAAGAGCCCGGGCGGATCTATGGATTACAAGGATGACGACGA

TAAGAGCCCGGGCGGATCTATGGATTACAAGGATGACGACGATAAGAGCC

CGGGCGGATCTATGGATTACAAGGATGACGACGATAAGAGCCCGGGCGGA

TCCGCGATACCGGAATTCCGGAATCCGCTCGAGCAATTGATGC-3'
``` ii) The synthetic DNA fragment is digested with NheI (NEB, R0131L) and MfeI (NEB, R0589L) and connected with plasmid pSicoR (Addgene, #67884) which is digested with NheI and EcoRI (NEB, R0101L) to obtain psi-Flag vector.

3) Construction of HA-ASK1$_N$ and Myc-ASK1$_N$ Vectors for Co-Immunoprecipitation to Verify the Inhibitory Effect of the Target Polypeptide on N-Terminal Dimerization of ASK1

Construction of HA-ASK1N vector: N-terminal sequence of ASK1 (NCBI: BC088829) gene is amplified by using the upstream primer: 5'-CGGGATCCATGAGCACGGAG-GCGGACGA-3' (SEQ. ID. NO: 16) and downstream primer: 5'-TGCGGCCGCTCAATCATATTCATAGTCAT- ACTCCAGC-3' (SEQ. ID. NO: 17), the amplified product and the pcDNA5-HA vector are digested with the restriction endonucleases BamHI and NotI (NEB, R0189L) and connected to obtain the HA-ASK1$_N$ vector.

Construction of Myc-ASK1$_N$ vector: N-terminal sequence of ASK1 (NCBI: BC088829) gene is amplified by using the upstream primer: 5'-GAAGATCTATGAGCACGGAG-GCGGACGA-3' (SEQ. ID. NO: 18) and downstream primer: 5'-CATGCCATGGTCAATCATATTCATAGTCAT-ACTCCAGC-3' (SEQ. ID. NO: 19), the amplified product and the pcDNA5-Myc vector are digested with the restriction endonucleases BglII (NEB, R0144L) and NcoI (NEB, R0193L) and connected to obtain the Myc-ASK1$_N$ vector.

4) Construction of Candidate Polypeptide Vectors the amino acid sequence of the polypeptides used in this patent are as follows:

```
Peptide 1 (SEQ. ID. NO: 20):
LHNGRSKEQRLKEQLGAQQEPVKKSIQESEAFLPQSIPEERYKMKSKPLG
ICLIIDCI Peptide2 (SEQ. ID. NO: 21):
MSAEVIHQVEEALDTDEKEMLLFLCRDVAIDVVPPNVRDLLDILRERGKL
SVGDLAEL Peptide3 (SEQ. ID. NO: 22):
MVSKGEELFTGVVPILVELDGDVNGHKFSVSGEGEGDATYGKLTLKFICT
TGKLPVPW Peptide4 (SEQ. ID. NO: 23):
GVQCFSRYPDHMKQHDFFKSAMPEGYVQERTIFFKDDGNYKTRAEVKFEG
DTLVNRIE
``` i) The Peptide1 fragment is amplified using the cFLIP (NCBI: NM_003879.5) cDNA as a template, the primer pairs are as follows:

```
Forward:
                            (SEQ. ID. NO: 24)
5'-CGGGATCCCTCCATAATGGGAGAAG-3

Reverse:
                            (SEQ. ID. NO: 25)
5'-GCTCTAGAAATGCAATCGATTATC-3';
``` ii) The Peptide2 fragment is amplified using the cFLIP (NCBI: NM_003879.5) cDNA as a template, the primer pairs are as follows:

```
Forward:
                            (SEQ. ID. NO: 26)
5'-CGGGATCCATGTCTGCTGAAGTC-3

Reverse:
                            (SEQ. ID. NO: 27)
5'-GCTCTAGATCACAGTTCAGCCAAGTC-3';
``` iii) The Peptide3 fragment is amplified using the GFP (NCBI: KX130867.1) cDNA as a template, the primer pairs are as follows:

```
Forward:
                            (SEQ. ID. NO: 28)
5'-CGGGATCCATGGTGAGCAAGGGCG-3

Reverse:
                            (SEQ. ID. NO: 29)
5'-GCTCTAGATCACCAGGGCACGGGCAG-3';
``` iv) The Peptide4 fragment is amplified using the GFP (NCBI: KX130867.1) cDNA as a template, the primer pairs are as follows

```
Forward:
                            (SEQ. ID. NO: 30)
5'-CGGGATCCGGCGTGCAGTGCTTC-3

Reverse:
                            (SEQ. ID. NO: 31)
5'-GCTCTAGATCACTCGATGCGGTTCAC-3';
``` v) The psi-flag vector and the amplified target gene are digested with the restriction endonucleases BamH I and Xba I, and then connected to obtain the psi-flag-peptides (Flag-peptides) vectors.

(3) Construction of Mammalian Two-Hybrid Screening System

1) The constructed ASK1$_N$ mammalian two-hybrid detection vector is packaged with virus in HEK-293T cells for 72 h, and the medium is collected and used for infection;

2) The HEK-293T cells are cultured in 6-well plates for 18-24 hrs so that the number of cells reach to $2 \times 10^5$ per hole;

3) The next day, the original medium is replaced with 2 ml fresh medium containing 6 µg/mL polybrene, and an appropriate amount of virus suspension is added;

4) After 48 h of continuous culture, the virus-containing medium is replaced with fresh medium, and the polypeptide plasmids to be screened is transfected.

(4) Polypeptide Plasmids Transfection

1) Configure the transfection solution as follows:

A) 0.5 µg psi-Flag-Peptides+0.5 µg pG5luc plasmid is added to 200 µL serum-free DMEM medium and is mixed even by vortex oscillation;

B) TurboFect transfection reagent is mixed by vortex oscillation slightly, 2 µL mixture is added to the medium of a, blown and mixed immediately, and then placed at room temperature for 20 min;

2) The transfected solution is added to a 24-well culture plate that culture HEK-293T cells which expressed pACT-ASK1$_N$ and pBIND-ASK1$_N$ vectors stably, and then shake to mix and incubate at 37° C. for 24 hrs.

(5) Luciferase Fluorescence Detection

1) Cell lysis: discard the medium and cells are lysed with reporter gene lysis buffer. After full lysis, the resulting solution is centrifuged at 10,000-15,000 g for 3-5 min to collect supernatant;

2) Dissolve the firefly luciferase detection reagent and *Renilla* luciferase detection buffer, and reach room temperature, the *Renilla* luciferase detection substrate (100×) is placed in an ice bath or ice box;

3) *Renilla* luciferase assay substrate (100×) is diluted (1:100) with *Renilla* luciferase detection buffer;

4) Turn on the fluorescence meter (Promega, GloMax® 20/20 Luminometer), and set the detection interval to 2 s, and the detection time to 10 s.

5) When each sample is detected, take 20-100 µL of the sample and add 100 µL firefly luciferase detection reagent, then detecting the RLU (relative light unit) after mixing with a gun, wherein the reporter gene cell lysate is used as blank control;

6) After completing the step of detecting the firefly luciferase, add 100 µL *Renilla* luciferase detection solution, and mix it with the gun to detect the RLU (relative light unit);

7) In the case of *Renilla* luciferase as the internal reference. Inhibition degrees of the different polypeptides are compared according to the obtained ratio of RLU value of firefly luciferase and *Renilla* luciferase.

(6) Co-Immunoprecipitation

1) The HEK-293T cells are transfected with the constructed plasmids HA-ASK1N and Myc-ASK1N respectively or simultaneously. The plasmids psi-flag-Peptides are then transfected into HEK-293T cells containing both HA-ASK1N and Myc-ASK1N, respectively.

2) The cells are harvested after transfection for 24 hrs, add the appropriate amount of cell lysis buffer (containing protease inhibitor), lysate on ice for 30 min, take the supernatant after cell lysate is centrifuged at 4° C. with the maximum speed for 30 min;

3) Take a small amount of lysate for Western blot assay, add 1 μg of anti-HA antibody (Sigma, # H6908) to the remaining lysate, and slowly shake and incubate overnight at 4° C.;

4) Take 10 μL protein A/G agarose beads (11719394001 and 11719386001, Roche), wash 3 times with the appropriate amount of lysis buffer and centrifuge at 3,000 rpm for 3 min per time;

5) Add the pretreated 10 μL protein A/G agarose beads to the cell lysate that incubated overnight with antibodies, and slowly shake and incubate at 4° C. for 2-4 hrs to equilibrate the antibodies with protein A/G agarose beads;

6) After the co-immunoprecipitation reaction, centrifuge at 4° C. with 3,000 rpm for 3 min until the agarose beads are centrifuged to the bottom of the tube; aspirate the supernatant, and wash the agarose beads 3-4 times with 1 ml lysis buffer; finally add 15 pt of 2×SDS loading buffer, and boil in boiling water for 5 min;

7) SDS-PAGE, Western blot assay.

(7) Western Blot

1) Protein Extraction

Add lysis buffer to cultured cells, collect the protein samples and quantitatively using the BCA Protein Assay Kit.

2) Electrophoresis i) Place the prepared gel plate in the electrophoresis tank, and the electrophoretic internal solution and the electrophoretic outer solution are added. Each electrophoresis tank contains 200 ml electrophoretic internal solution and the electrophoresis tank is filled with the electrophoretic outer solution with ⅔ of the volume of the electrophoresis tank.

ii) Load the protein sample into the sample hole of SDS-PAGE gel, and start the electrophoresis.

3) Transfer i) Prepare the transfer buffer and place at 4° C. for precooling.

ii) Cut the PVDF membrane by 8 cm×5.9 cm and cut a gap in the corner as the upper left corner of the membrane, before use, soak it in methanol for 15 s and then put it in the transfer buffer.

iii) Spread the splint around and turn the negative to the right. The black side is negative, and the white side is positive, and both sides are covered with two sponges and five filter papers (the sponges and filter papers are previously wetted with transfer buffer).

iv) Remove the gel in the gel plate, remove the excess part, wash the gel with the transfer buffer, place the gel on the filter paper of the negative electrode, remove the air bubbles, cover it with the PVDF membrane, make the gap align with the corner of the largest marker, and remove the bubbles and cover the left filter paper and sponge (cannot have bubbles), and clip the splint.

v) Place the splint in the transferring film groove and the negative (black face) of the transferring film groove should be placed together with the negative (black side) of the splint, fill the transfer buffer to flood the gel.

vi) Connect the transferring film groove to the power supply. Transfer in transfer buffer at 250V and 0.2 A for 1.5 h.

vii) Take out the PVDF membrane after the transfer.

4) Sealing

Wash the membrane with TBST buffer. Put the membrane in sealing solution for 1-4 hrs on a slowly shaking platform at room temperature to block no-specific binding.

5) Primary Antibody Incubation i) Wash the membrane 3 times for 5 min each with TBST.

ii) The sealing machine seals the film into the hybrid bag, add a primary antibody, not leaving the air as far as possible.

iii) Place the hybrid bag in the shaking table at 4° C. for overnight.

6) Secondary Antibody Incubation i) Take out and wash the membrane 3 times for 5 min each with TB ST.

ii) Incubate the membrane with corresponding secondary antibody for 1 h in dark.

7) Protein Detection

After incubation, wash the membrane 3 times again for 5 min each with TBST. The target bands are detected using a Bio-Rad Chemi Doc XRS$^+$ gel imaging system.

(8) Construction of Adeno-Associated Virus Vector System (AAV8-GFP-Peptide1/AAV8-GFP)

AAV8 is a liver-targeted gene therapy vector, and the in the present disclosure is used for mediating the overexpression of Peptide1 in liver of cynomolgus monkeys (*Macaca. fascicularis*) to study the effect of Peptide1 overexpression on nonalcoholic steatohepatitis.

1) The plasmid PX458 (Addgene, 48138) is used as template to amplified T2A-EGFP fragment, and the primer pairs are as follows:

```
PX458-HindIII-F:
                                    (SEQ. ID. NO: 32)
(CCCAAGCTTGGTACCACTAGTGTCGACgaattcGGCAGTGGAGAGGG)
PX458-BgLII-R:
                                    (SEQ. ID. NO: 33)
(GGAAGATCTTTACTTGTACAGCTCGTCCATGCC).
```

The T2A-EGFP fragment is connected with pAAV-MCS (AAV vector) that digested with HindIII and BgLII (NEB, R0144L) to construct the pAAV-T2A-EGFP vector.

The following sequences are synthesized and:

```
MCS-Oligo1-SacI:
                                    (SEQ. ID. NO: 34)
(CtctagactcgagaccggtCTTAAGGCTAGCGATATCGGATCCAAGCTT
GGTAC)

MCS-Oligo2-KpnI:
                                    (SEQ. ID. NO: 35)
(CAAGCTTGGATCCGATATCGCTAGCCTTAAGACCGGTCTCGAGTCTAGA
GAGCT)
```

The synthetic DNA fragments are annealed and pAAV-MCS-T2A-EGFP vector is constructed by connecting the annealed products with pAAV-T2A-EGFP vector which digested with SacI (NEB, R0156L) and KpnI (NEB, R0142L).

2) The cDNA of gene cFLIP (NCBI: NM_003879.5) is used as template to amplified to amplified Peptide1 encoding sequence, the primer pairs are as follows:

Upstream primer:
(SEQ. ID. NO: 7)
5'-GCTCTAGAgccaccATGCTCCATAATGGGAGAAG-3'

Downstream primer:
(SEQ. ID. NO: 8)
5'-CGGGATCCCTTGTCATCGTCGTCCTTGTAATCAATGC The Peptide1 encoding sequence is digested with XbaI and BamHI, then subcloned to a pAAV-MCS-T2A-EGFP vector which is digested with the same enzymes to obtain a pAAV-Peptide1-T2A-EGFP vector in which the fragment Peptide1 is located in the same reading frame with EGFP, leading to the co-expression of Peptide1 and EGFP, thereby facilitating section observation.

3) Three plasmid transfection systems (pAAV-Peptide1-T2A-EGFP, pAAV-Helper and pAAV-2/8) are co-transfected into AAV293 cells using PEI (Polysciences cat #24765) and incubated for 72 h. Then the cells are collected and ultrasonically lysed, centrifuging to remove cell debris (for the AAV8-GFP control group, pAAV-MCS-T2A-EGFP, pAAV-Helper and pAAV-2/8 are used as plasmid transfection systems).

4) The virus is purified by cesium chloride gradient centrifugation and then separated with 1×PBS+5% Sorbitolin Slide-A-Lyzer dialysis cassettes to remove cesium chloride, to obtain adeno-associated virus AAV8-GFP-Peptide1 and AAV8-GFP.

5) The Virus titer analysis is performed by fluorescent quantitative PCR, comprising the following steps:

a. Add 10 µL purified virus solution into 100 µL DNase lysate (10 mM Tris.Cl, pH 7.5, 10 mM $MgCl_2$, 2 mM $CaCl_2$, 50 U/ml DNase I) and incubate at 37° C. for 1 h;

b. Add 0.5 M EDTA and mix evenly, incubate at 70° C. for 10 min, and then add protease K (50 µg/ml), and incubate at 50° C. for overnight.

c. Incubate at 99° C. for 10 min to deactivate protease K completely. Add sterile double-distilled water up to 1 ml, collect a 2 µL sample, and add water up to 400 µL to obtain a template for fluorescence quantitative PCR;

d. Dilute plasmid pAAV-Peptide1-T2A-EGFP/pAAV-MCS-T2A-EGFP to eight concentration gradients of $5\times10^1$ to $5\times10^8$ to make standard substances.

e. Collect a 2 µL sample and a 2 µL standard substance respectively, perform fluorescence quantitative PCR using GFP-specific primers: Forward 5'-AGCAGCACGACTTCTTCAAGTCC-3' (SEQ. ID. NO: 36) and Reverse 5'-TGTAGTTGTACTCCA GCTTGTGC-3' (SEQ. ID. NO: 37). Calculate the copy number of vectors in viruses (virus titer) according to the standard curve defined by the standard substance.

Example 1 Screening of Peptides that can Inhibit N-Terminal Dimerization of ASK1

HEK-293T cells that expressing p pACT-ASK1$_N$ and pBIND-ASK1$_N$ plasmids stably are divided into five groups, named as groups A, B, C, D, and E. Among these groups, cells of group A are infected with pG5luc plasmid only. In groups B, C, D, and E, HEK-293T cells are transfected into both plasmid pG5luc and one of psi-flag-Peptide 1, psi-flag-Peptide 2, psi-flag-Peptide 3, and psi-flag-Peptide 4 respectively. The five groups are as follows:

A: HEK-293T cells (pACT-ASK1$_N$+pBIND-ASK1$_N$)+pG5luc

B: HEK-293T cells (pACT-ASK1$_N$+pBIND-ASK1$_N$)+psi-flag-Peptide 1+pG5luc

C: HEK-293T cells (pACT-ASK1$_N$+pBIND-ASK1$_N$)+psi-flag-Peptide 2+pG5luc

D: HEK-293T cells (pACT-ASK1$_N$+pBIND-ASK1$_N$)+psi-flag-Peptide 3+pG5luc

E: HEK-293T cells (pACT-ASK1$_N$+pBIND-ASK1$_N$)+psi-flag-Peptide 4+pG5luc

After the transfection solutions are added, the cells are incubated at 37° C. for 24 hrs and then collected for Luciferase fluorescence assay.

The results of fluorescence assay shown in FIG. 1. Group A (free of plasmid psi-flag-Peptide) shows normal N-terminal dimerization of ASK1, with the ratio of RLU value of firefly luciferase to RLU value of *Renilla* luciferase is about 1.9. In group B, the ratio of RLU value of firefly luciferase to RLU value of *Renilla* luciferase is significantly lower as compared with peptide-free group, indicating that Peptide1 inhibits N-terminal dimerization of ASK1. In group C, D, and E, there is no significant difference as compared with group A, indicating that Peptide 2, 3, 4 have no effect on N-terminal dimerization of ASK1.

Example 2 Evaluation of Inhibitory Effect of Peptides on N-Terminal Dimerization of ASK1 by Immunoprecipitation Assay HEK-293T cells are divided into seven groups, named as groups A, B, C, D, E, F, and G. Among these groups, only vector HA-ASK1$_N$ or Myc-ASK1$_N$ is transfected into cells in groups A and B, both vectors HA-ASK1$_N$ and Myc-ASK1$_N$ are transfected into cells in groups C, D, E, F, and G, and positive cells are screen after 48 h incubation. The obtained cells are as follows:

Group A: HEK-293T cells (HA-ASK1$_N$)
Group B: HEK-293T cells (Myc-ASK1$_N$)
Groups C, D, E, F, and G: HEK-293T cells (HA-ASK1$_N$+Myc-ASK1$_N$)

Then the transient transfection of target peptide plasmids is performed, only an equal amount of transfection buffer free of target peptide plasmid is added to the cells in groups A, B, and C respectively, and transfection buffer containing plasmid psi-flag-Peptide1, psi-flag-Peptide2, psi-flag-Peptide3 or psi-flag-Peptide4 is added to the cells in groups D, E, F, and G respectively, that is, the seven groups are as follows:

Group A: HEK-293T cells (HA-ASK1$_N$)
Group B: HEK-293T cells (Myc-ASK1$_N$)
Group C: HEK-293T cells (HA-ASK1$_N$+Myc-ASK1$_N$)
Group D: HEK-293T cells (HA-ASK1$_N$+Myc-ASK1$_N$)+psi-flag-Peptide 1
Group E: HEK-293T cells (HA-ASK1$_N$+Myc-ASK1$_N$)+psi-flag-Peptide 2
Group F: HEK-293T cells (HA-ASK1$_N$+Myc-ASK1$_N$)+psi-flag-Peptide 3
Group G: HEK-293T cells (HA-ASK1$_N$+Myc-ASK1$_N$)+psi-flag-Peptide 4

The cells are harvested after 24 hrs transfection and subjected to immunoprecipitation assay for evaluating the effect of the target peptide on N-terminal dimerization of ASK1. In Western blot assay, the primary antibodies used: HA (Sigam, #H6908), Myc (MBL, #M192-3), Flag (Sigma, #F3165), the secondary antibodies used: HRP AffiniPure Goat Anti-Rabbit IgG (H+L) (Jackson, #111-035-003), Biotin AffiniPure Goat Anti-Mouse IgG (H+L) (Abbkine, A21210).

During immunoprecipitation assay, protein A/G agarose beads are bound with HA-ASK1$_N$ in the cell lysates via HA antibody. In the case of normal N-terminal dimerization of ASK1, HA-ASK1$_N$ and Myc-ASK1$_N$ are contained in the protein solution obtained from immunoprecipitation, causing two stripes of HA-ASK1$_N$ and Myc-ASK1$_N$ shown in the Western blot pattern. In the case of inhibited N-terminal dimerization of ASK1, the content of Myc-ASK1$_N$ is significantly reduced, even to be undetectable.

Figure 2:
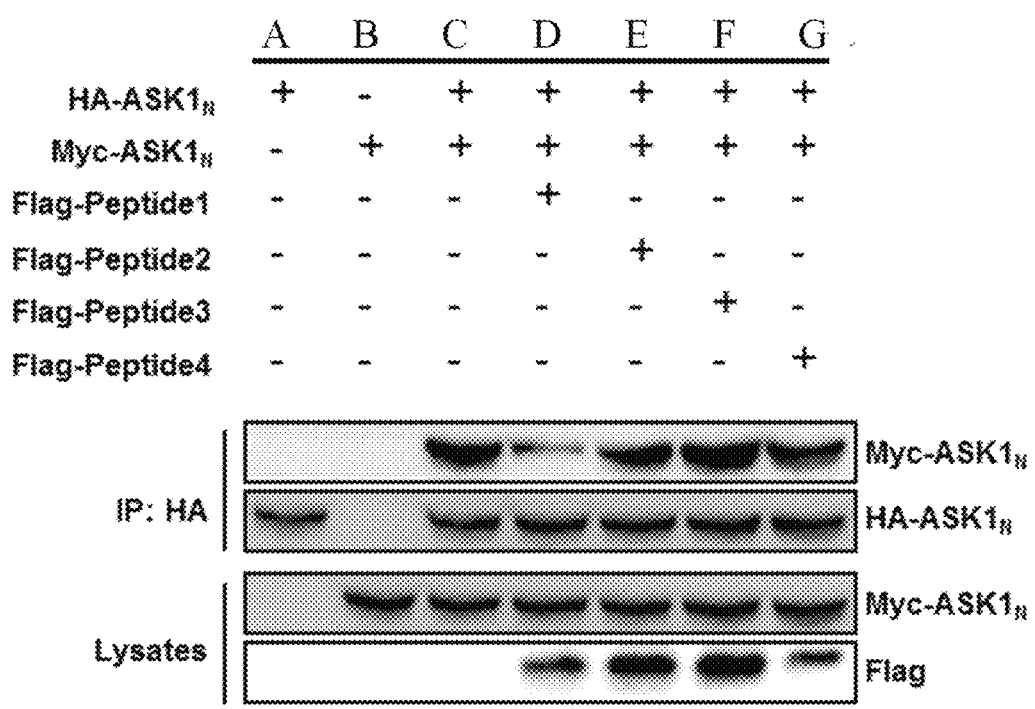
FIG. 2 is a detection result of Western blot assay of lysate of HEK-293T cells which have been transfected with different plasmids and a protein solution obtained by co-immunoprecipitation.

The results of Western blotting shown in FIG. 2 indicates that groups B-G show normal same expression level of Myc-ASK1$_N$ in the cells, groups D-G show same expression level of different peptides in the cells. After immunoprecipitation, the results of Western blotting indicate that group A shows a clearly visible strip of HA-ASK1$_N$, group B shows no obvious strips, group C shows two clearly visible strips, groups E, F, and G show the same result with group C, showing no inhibition of N-terminal dimerization of ASK1. While group D shows significantly weakened strip of Myc-ASK1$_N$ in the case of Peptide1 involved, with strip of HA-ASK1$_N$ being unchanged, further indicating that Peptide1 can inhibit N-terminal dimerization of ASK1.

Example 3 Inhibition of ASK1-JNK1 Signaling Pathway by Inhibiting N-Terminal Dimerization of ASK1

The effect of inhibited N-terminal dimerization of ASK1 on intracellular JNK1 signaling pathway is evaluated by Western blot assay. The primary antibodies required: p-ASK1 (Cell Signaling Technology, #3765), ASK1 (GeneTex, # GTX107921), p-MKK7 (Aviva Systems Biology, # OAAF05547), MKK7 (Cell Signaling Technology, # 4172), p-JNK1 (NOVUS, # NB100-82009), JNK1 (Abcam, # ab199380), Flag (Sigma, # F3165); the secondary antibodies required: HRP AffiniPure Goat Anti-Rabbit IgG (H+L) (Jackson, #111-035-003), Biotin AffiniPure Goat Anti-Mouse IgG (H+L) (Abbkine, A21210).

Figure 3:
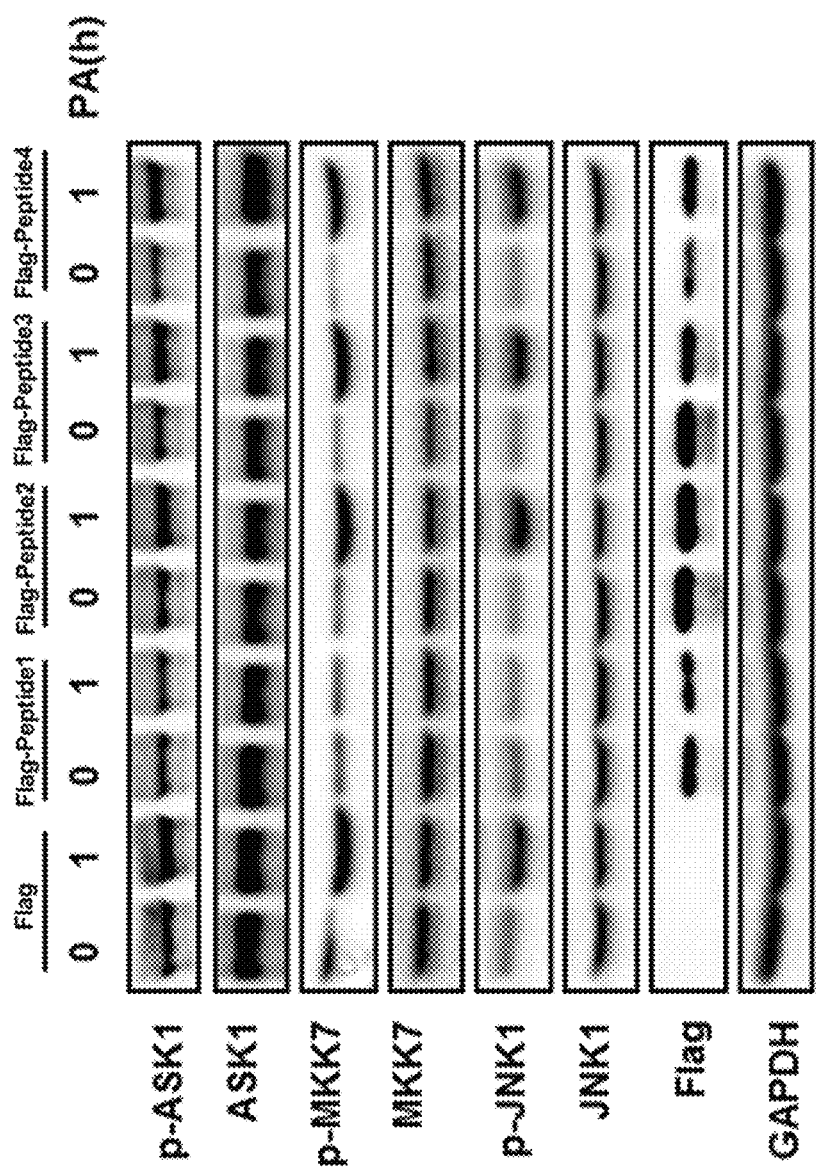
FIG. 3 is a detection result of Western blot assay of ASK1-JNK1 signaling pathway in L02 cells transfected with different polypeptide plasmids after stimulation with PA for 1 h.

L02 cells are divided into five groups (numbered as groups A, B, C, D, and E) and cultured at 37° C. until the cell density reaches to 70%. Cells in Group A are transfected with plasmid psi-flag, to serve as a control. Cells in Group B, C, D, and E are transfected with plasmid psi-Flag-Peptides 1, 2, 3, or 4 respectively. After 24 hrs incubation, a palmitate (PA) is added to culture medium of each group and incubate for 1 h, BSA is served as a control. Cells are collected for Western blot to assay the changes in the expression of individual proteins involved in intracellular ASK1-JNK1 signaling pathway. As shown in FIG. 3, the results show that there is no significant change in the expression level of Flag protein in each group, indicating that the expression levels of different peptides are substantially consistent. Among the groups, group B shows no significant increase of expression level of proteins p-ASK1, p-MKK7, and p-JNK1 compared with the BSA control, that is, the inhibition of N-terminal dimerization of ASK1 can inhibit the phosphorylation of ASK1, MKK7 and JNK1 and inhibit ASK1-JNK1 signaling pathway.

Example 4 Effects of Promoting Cell Lipid Metabolism and Inhibiting Steatohepatitis by Inhibiting N-Terminal Dimerization of ASK1

Figure 4A:
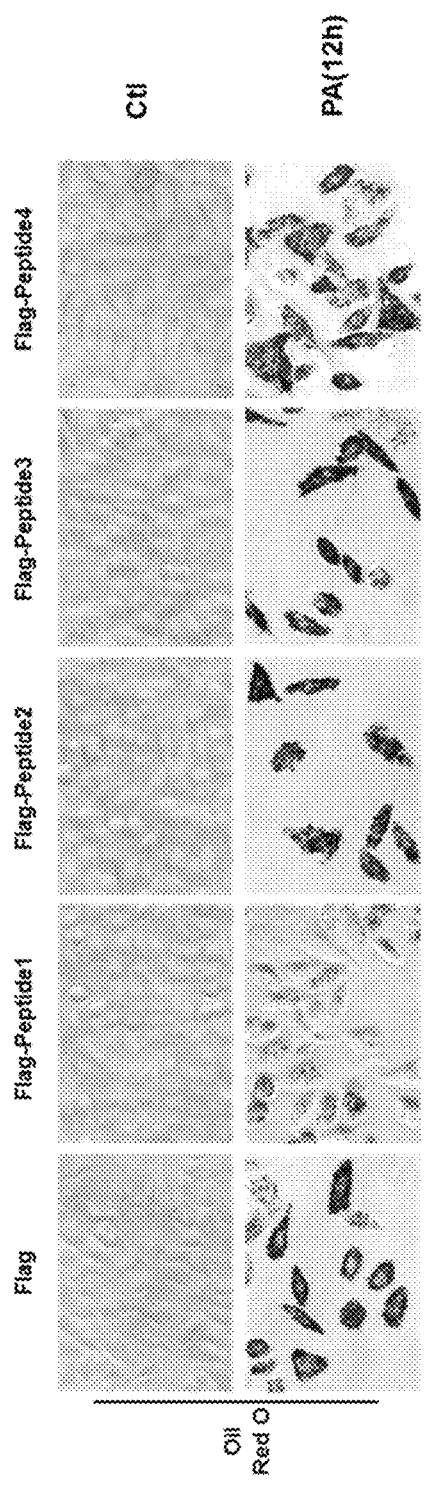
Figure 4B:
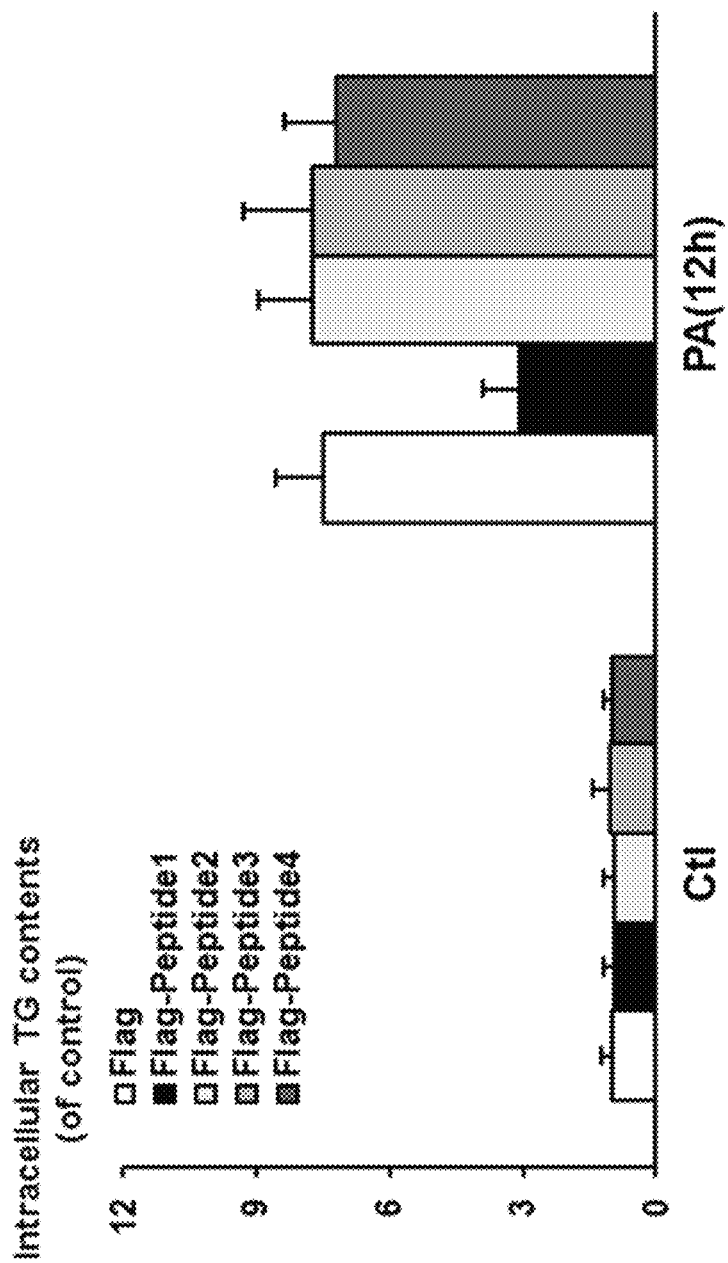

L02 cells are divided into five groups (numbered as groups A, B, C, D and E). Cells in Group A are transfected with plasmid psi-flag, serving as a control, and cells in Group B, C, D and E are transfected with plasmids psi-Flag-Peptides1, psi-Flag-Peptides2, psi-Flag-Peptides3 or psi-Flag-Peptides4, respectively. After 24 hrs incubation, PA is added to culture medium and incubate for 12 h, BSA is served as a control (Ctl). Then oil red O staining is performed, and the content of intracellular triglyceride is detected using a triglyceride assay kit (colorimetry) (Cayman, 10010303). The relative values of intracellular triglyceride content of other groups are calculated on the basis of setting the content of intracellular triglyceride in BAS control cells of Group A as 1. The procedure of oil red O staining comprises the following steps:

(1) washing the sample group and control group with 1×PBS twice, and fixing with 300 µL 3% paraformaldehyde for 20 min;

(2) washing with 1×PBS twice, and rinsing with 60% isopropanol for 10 s;

(3) washing with 1×PBS twice, and blow-drying in a ventilating cabinet;

(4) adding 500 µL oil red O stain in each well and staining for 1 h;

(5) washing with 1×PBS twice, fractioning with 60% isopropanol and washing again with 1×PBS twice; detecting under a microscope and imaging;

As shown in FIGS. 4A-4B (FIG. 4A is an oil red O staining graph), a lot of cells in Group A are stained in red, indicating that after PA exposure for 12 h, there is obvious lipid deposition in the cells; The results of cell staining of Group C, D and E are similar to Group A, showing a large area of red stained cells in each group. While in Group B, in the case of Peptide1 expression in cells, there are less oil red O stained cell and smaller staining area in cells after PA exposure for 12 h. As shown in FIG. 4B (a view of detection results of intracellular relative triglyceride content), the contents of intracellular triglyceride in the BSA-treated controls are lower, and there is no significant difference in triglyceride content among the five groups. However, after 12 h PA treatment, the contents of intracellular triglyceride are significantly increased as compared with the controls of each group, and the increase in content of intracellular triglyceride of Flag-Peptide1-transfected Group B is smallest as compared with other groups. The results indicate that Peptide1 can inhibit steatosis of liver cells by inhibiting N-terminal dimerization of ASK1, and N-terminal dimerization of ASK1 is significant in the screening of drugs against steatohepatitis and can be used as a potential therapeutic target for treatment of steatohepatitis disorders.

Example 5 Construction of Cynomolgus Monkey Model of AAV8-Peptide1-Mediated Liver Over-Expression of Peptide1

Cynomolgus monkeys are given an AAV8-Peptide1 vector by portal venous injection, for over-expression of Peptide1 in the liver.

Cynomolgus monkeys are fed with a high-fat diet (provided by Beijing Huafukang bioscience Co. Ltd., batch No. #5043, calorie ingredients: proteins: 17.86%, carbohydrates: 58.8%, fats: 22.34%) for 2 d, and then randomly divided into three groups (6-8 monkeys each group) that are injected with AAV8-GFP-Peptide1, AAV8-GFP and normal saline, respectively. Portal vein injection requires laparotomy, with preoperative fasting 10-14 hrs and water deprivation 6 h. Before surgery, monkeys receive intramuscular injection of atropine 0.05 mg/kg (for reducing gland secretion during surgery) and about 10 min later, receive intramuscular injection of Shumianning II 0.1 ml/kg. After anesthetization, the monkeys undergo body weighing and skin preparation, are fixed in supine position on an operating table and connected with an ECG monitor for monitoring blood oxygen saturation, blood pressure and heart rate. The abdominal cavity is opened by cutting along the middle line of abdomen, the portal vein is captured and then injected slowly with 1 ml of a buffer solution containing an AAV8-GFP-Peptide1 vector (titer of 5.88E+08 Tu/ml, serotype AAV2/8). Pressed with sterile gauzes for bleeding stopping, followed by suturing after determination of no bleeding. Penicillin (4 million units) is administered by intravenous drip infusion for infection control. The abdominal cavity is closed layer by layer, and the bellyband is worn for preventing postoperative excessive tension of incision and reducing intraperitoneal bleeding (AAV8-GFP group and normal saline group are injected with equal volumes of normal saline containing AAV8-GFP virus and normal saline, respectively, and investigated in the same way as AAV8-GFP-Peptide1 group). After high fat-feeding for 20 weeks, tissues are collected by needle biopsy, for immuno-fluorescence assay and Western blot assay of adeno-associated virus-mediated overexpression of Peptide1

Cynomolgus monkeys are fed with a high fat-diet #5043 and 150 g fruits every day for 30 weeks. All animals are given water.

Example 6 Inhibition of Incidence of Steatohepatitis Due to High Fat-Feed by Over-Expression of Peptide1 in Liver of Cynomolgus Monkeys The physiological indices of the experiment monkeys are detected every two weeks, including body weight, body temperature, breathing, heart rate, blood pressure, waist measurement, hip measurement, sitting height, etc. Abdominal ultrasonography is performed every four weeks. Blood samples (5 ml) are collected at Week 0 and Week 30 and subjected to serum separation, followed by detection of fasting serum lipid levels (triglyceride, total cholesterol, high-density lipoprotein and low-density lipoprotein) and liver functions (ALT, AST). The liver tissues are collected by needle biopsy, for fluorescence assay of GFP and Western blot assay of adeno-associated virus-mediated overexpression of Peptide1.

1. Fluorescence Assay and Western Blot Assay of Liver Tissues

Liver tissue frozen-slices are prepared and then observed under a fluorescence microscope for detecting green fluorescence intensity of GFP, to determine the efficiency of adeno-associated virus infection. Western blot assay of liver tissues is performed to detect the expression of Peptide1 in liver tissues.

(1) Liver Tissue Frozen-Slices

The tissues collected by biopsy are embedded in a freezing machine, and sliced (5 μm thick) after the embedding operation is completed, and the tissue slices are attached onto glass slides. The obtained frozen-slices are observed under a fluorescence microscope for detection of green fluorescence intensity.

(2) Western Blot Assay of Peptide1 Expression

1) Protein Extraction a. A liver tissue sample is collected under −80° C. temperature condition, and put in dry ice. 3-4 steel beads are put in each EP tube, and then the tubes are put in dry ice for pre-cooling. The sample is cut with ophthalmic scissors, the sample pieces are loaded to corresponding EP tubes, and the weight of the sample in each tube is recorded.

b. A lysis buffer is mixed with PMSF, and then a certain amount of the mixture is added to the samples and mixed evenly.

c. The samples are ground in a pre-cooled grinding machine adapter at −80° C., with the grinding parameter settings of 30 Hz/s, 90 s.

d. After the grinding operation is completed, the samples are put on ice for 10 min, and the steel beads are removed.

e. The samples are lysed using an ultrasonic lysis device at 5 KHz each time, is each time, every 1 second, over 10 times. After the ultrasonic lysis is completed, the samples are put on ice for 10 min.

f. The samples are centrifuged in a centrifuge (pre-cooled at 4° C.) under 12000 rpm/min at 4° C. for 30 min g. The supernatants are transferred to other EP tubes, and then centrifuged under 14000 rpm/min at 4° C. for 10 min.

h. The supernatants are transferred to other EP tubes, and then centrifuged under 14000 rpm/min at 4° C. for 5 min. The supernatants are collected and finely metered using BCA Protein Assay Kit (Pierec™, 23225).

2) According to the preceding steps, an SDS-PAGE gel column is prepared and loaded with the samples, followed by electrophoresis, membrane transfer, blocking, antibody incubation and protein detection. In the experiment, the primary antibody used is anti-Flag (Sigma, # F3165), and the secondary antibody is Biotin AffiniPure Goat Anti-Mouse IgG (H+L) (Abbkine, A21210).

2. Physiological and Biochemical Index Detection (1) Physiological Index Detection Monkeys are fasted 10-14 hrs with water deprivation for 6 h and then anesthetized by intramuscular injection of 10 mg/kg ketamine hydrochloride, and the above physiological indices are detected and the related experiment data are recorded.

(2) Biochemical Index Detection

Monkeys are fasted 10-14 hrs with water deprivation for 6 h before experiment, and anesthetized by intramuscular injection of 10 mg/kg ketamine hydrochloride, 5 ml blood samples are collected intravenously, and the samples are subjected to serum separation and delivered to Wuhan DiAn Diagnostics Company for detection of lipids contents and enzyme activities.

3. Liver Tissue Pathological Staining Related Experiments

Frozen slices and paraffin slices are prepared and subjected to oil red O staining and HE staining.

(1) Dehydration, Vitrification and Paraffin Embedding of Liver Organ

A liver tissue sample obtained by living biopsy is soaked in formaldehyde for fixation, a part of the well-fixed liver tissue sample is put in an embedding frame and washed with a small flow of flowing water for more than 30 min. The machine is set according to the following process: 1) dehydration: 75% ethanol (45 min)→75% ethanol (45 min)→85% ethanol (45 min)→85% ethanol (45 min)→95% ethanol (45 min)→95% ethanol (45 min)→anhydrous alcohol (1 h)→anhydrous alcohol (1 h); 2) vitrification: xylene (1 h)→xylene (1 h); 3) paraffin embedding (65° C.): paraffin (1 h)→paraffin (1 h). After the tissues are completely rinsed, the tissue embedding frame containing the tissues is put in the basket of the machine, and the above process is initiated. After the above procedures are completed, the tissues are embedded.

(2) Liver Tissue Slices

The liver tissue slices are prepared using a microtome (slice thickness of 5 μm).

(3) Hematoxylin-Eosin (HE) Staining of Liver Tissues

Put liver tissue paraffin slices in an oven at 65° C. (30 min)→xylene (5 min×3 times)→100% ethanol (1 min)→90% ethanol (1 min)→70% ethanol (1 min)→washing with distilled water→hematoxylin (5 min)→washing with tap water to remove excessive stains on the slices→1% hydrochloric acid ethanol solution (1-3 s)→washing with tap water for several times→Scott bluing solution (sodium bicarbonate 0.35 g, magnesium sulfate 2 g, distilled water 100 ml) (1 min)→washing with tap water for several times→Eosin dye (1 min)→washing with distilled water to remove excessive stains on the slices→70% ethanol once→90% ethanol once→100% ethanol (30 s×3 times)→xylene (2 min×3 times)→sealing before xylene volatiles to dry and imaging.

(4) Oil Red O Staining of Liver Tissues

1) Frozen liver tissue slices are air-dried for 30 min in a ventilating cabinet, and fixed with 4% paraformaldehyde for 10 min. The slices are soaked in double distilled water and washed for 10 min, to remove paraformaldehyde from tissue surface.

2) The slices are treated with 60% isopropanol for 1 min.

3) The slices are stained with oil red O (sigma, No. 00625, concentration of 0.5 g/100 ml 100% isopropanol) for 30 min.

4) Then the slices are rinsed with 60% isopropanol for 1 min for three times until the background is clean.

5) The slices are treated with Mayer's hematoxylin stain (5 droplets) for cell nucleus staining.

6) The slices are rinsed with water, then treated with diluted lithium carbonate aqueous solution and fully washed with water until 'blueness' color of cell nuclei.

7) The slices are sealed with glycerogelatin for imaging.

4. Tests

Figure 5A:
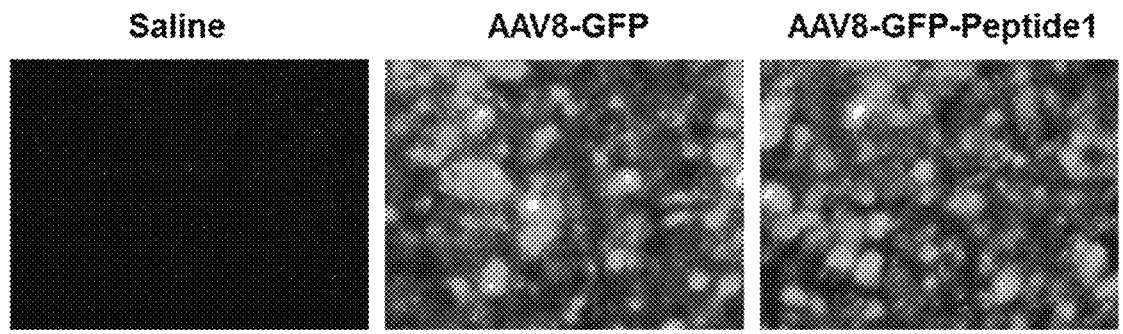
Figure 5B:
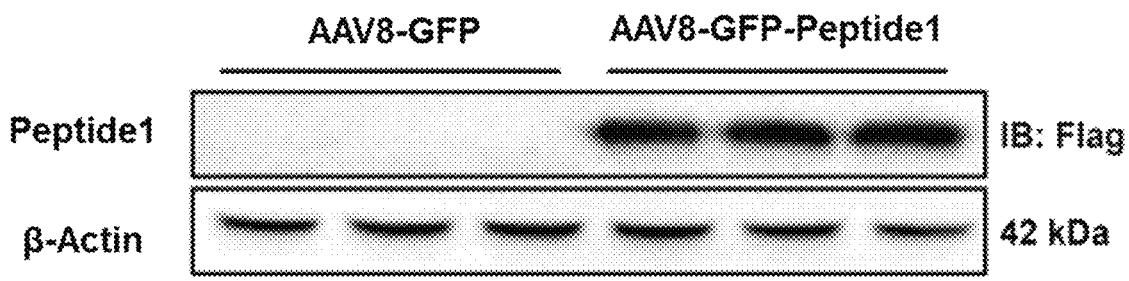

The results of fluorescence assay are shown in FIG. 5A. The liver tissues of monkeys in AAV8-GFP group and AAV8-Peptide1 group are found obvious green fluorescence under a fluorescence microscope, and there is no significant difference in fluorescence intensity between the two groups, indicating that the transfection rates of AAV8 vector in the monkey liver tissues of the two groups are the same. The results of Western blot are shown in FIG. 5B, AAV8-GFP group has no strips in Western blot pattern, indicating that the expression of Peptide1 is not found, while AAV8-Peptide1 group has obvious strips, indicating that the expression of Peptide1 peptide in the liver tissues of monkeys of AAV8-Peptide1 portal vein injection groups is significant.

Figure 6A:
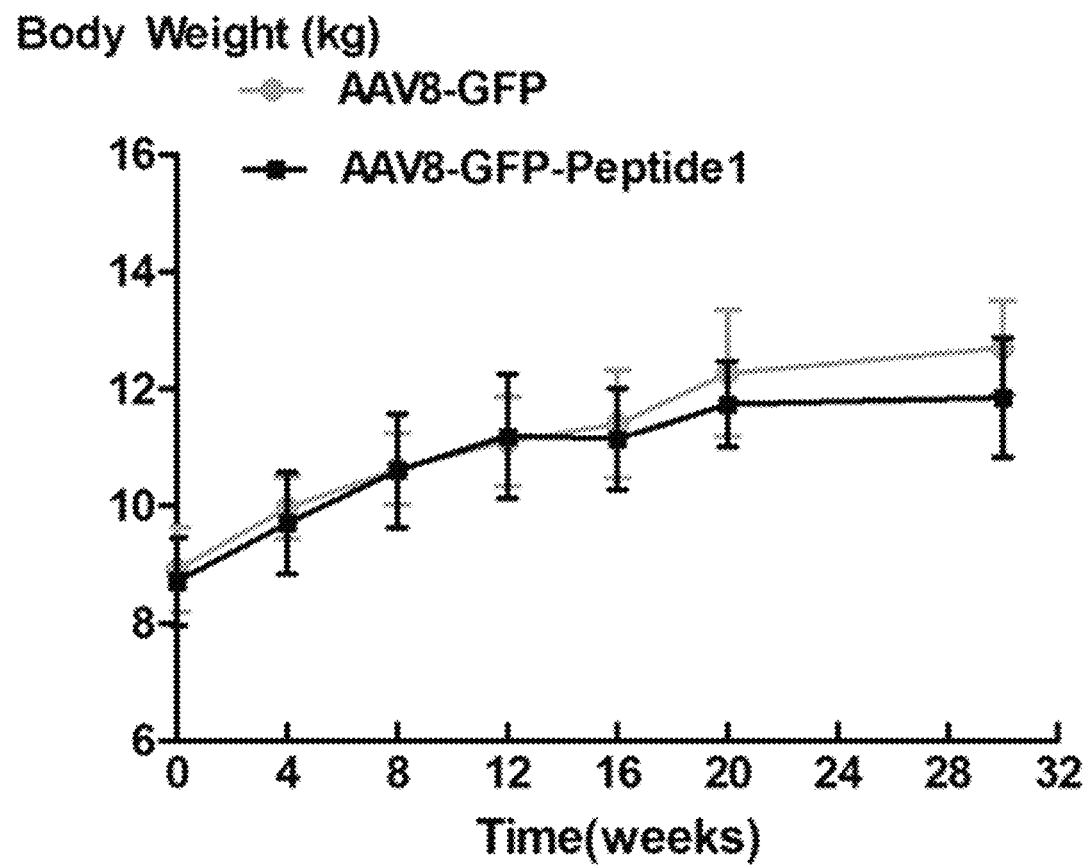
Figure 6B:
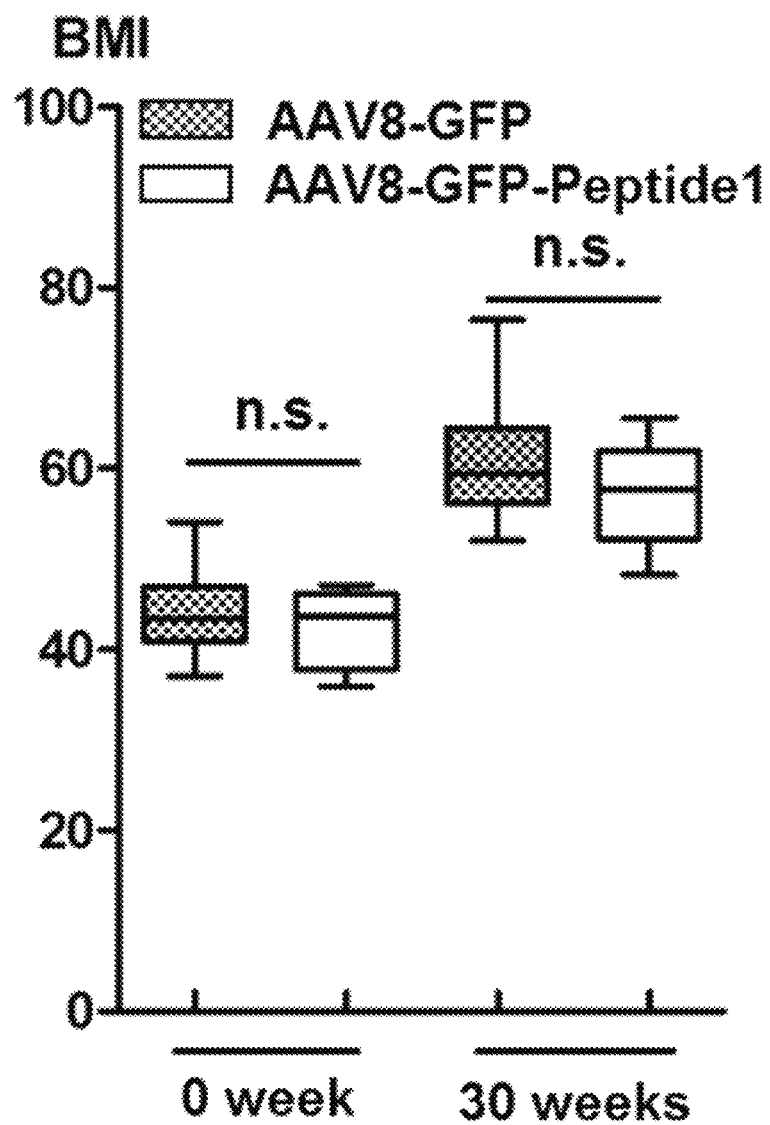

The data of body weight and BMI of the monkeys are shown in FIGS. 6A-6B. The Cynomolgus monkeys in AAV8-GFP group and AAV8-GFP-Peptide1 group are fed on a high-fat feed for 30 weeks from the beginning of experiment, there is no significant difference in body weight and BMI between the two groups (FIGS. 6A-6B).

Figure 7A:
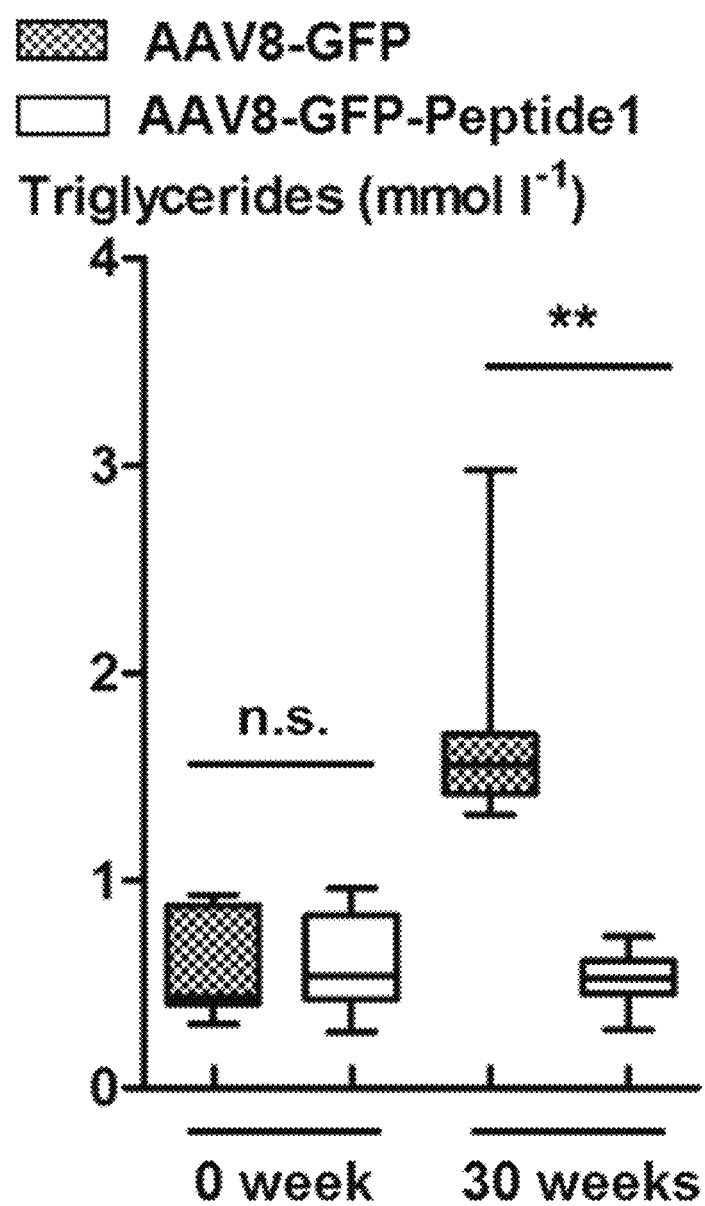
Figure 7B:
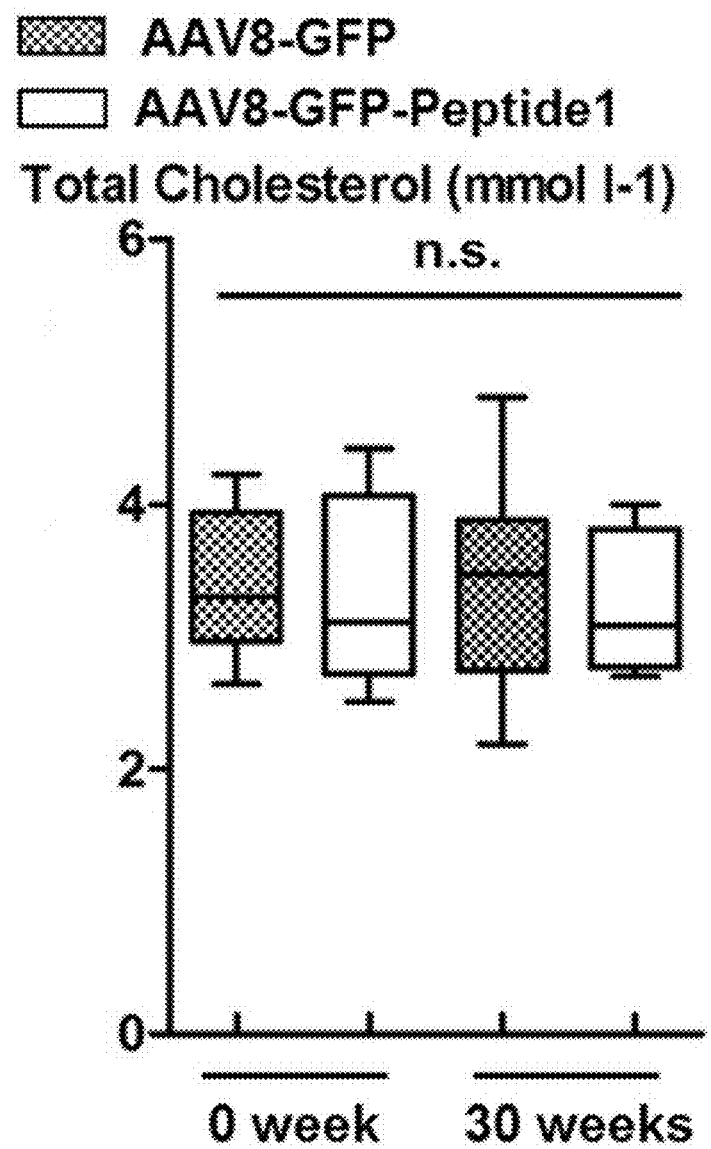
Figure 7C:
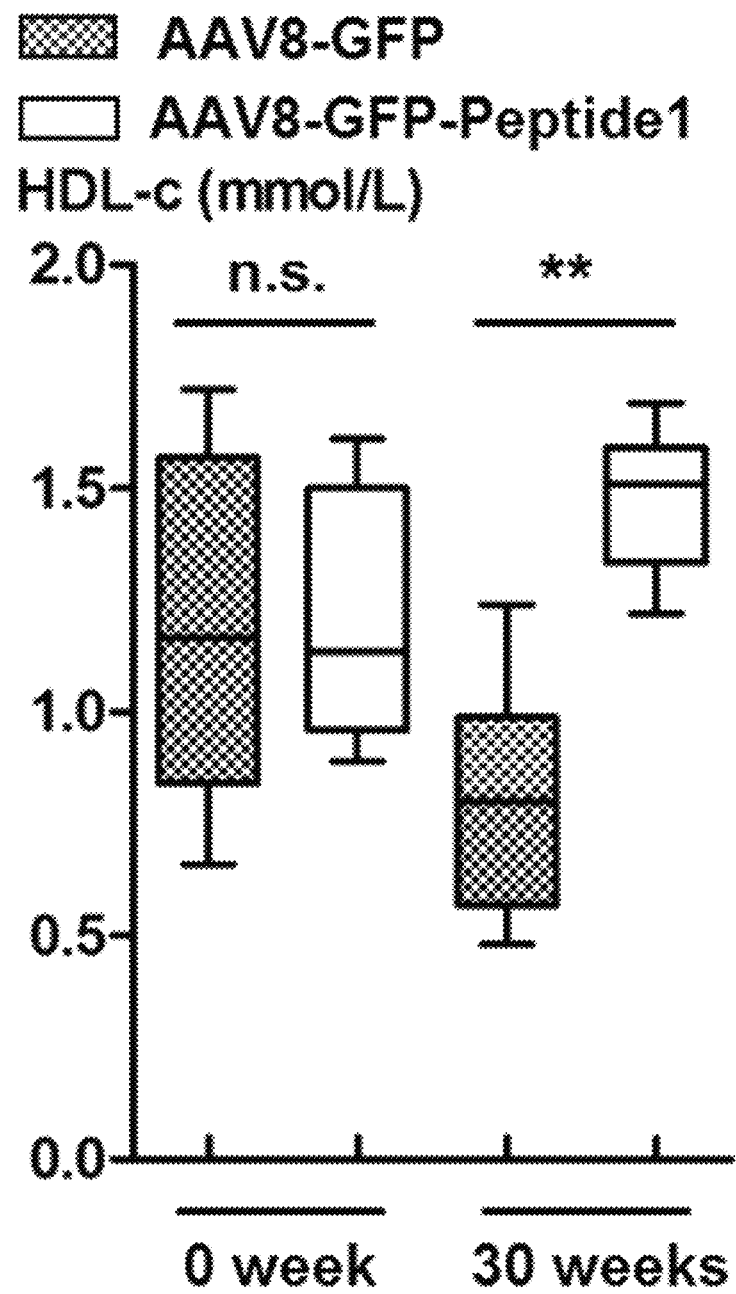
Figure 7D:
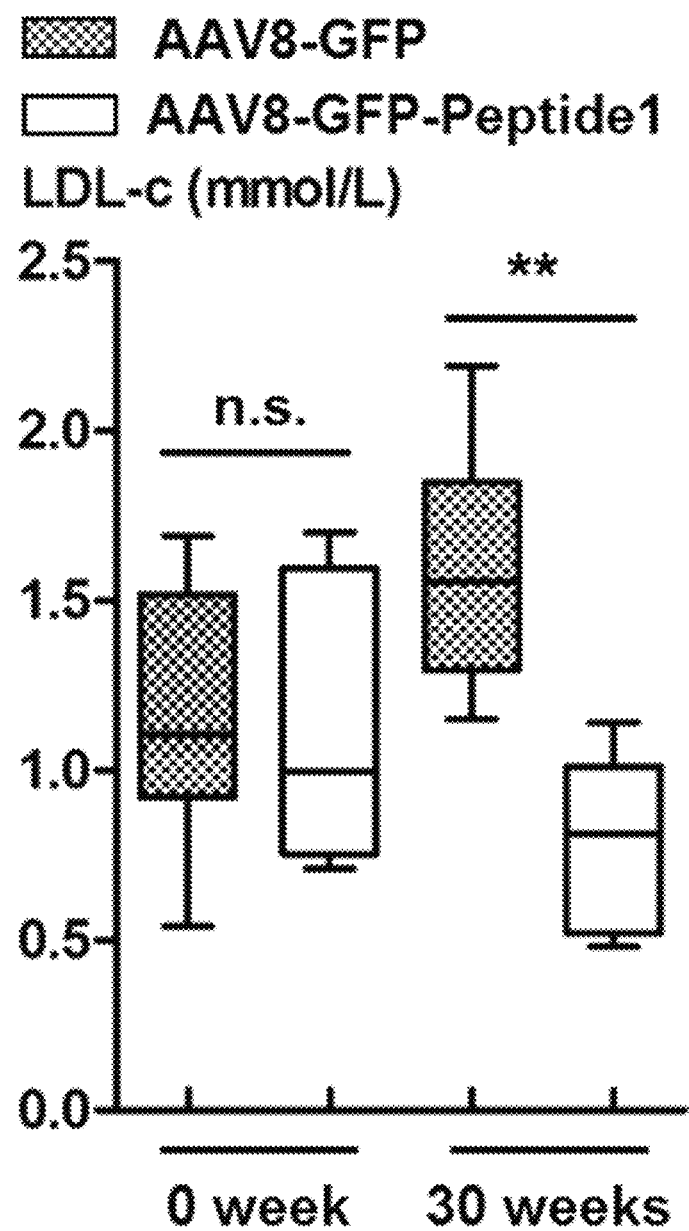
Figure 7E:
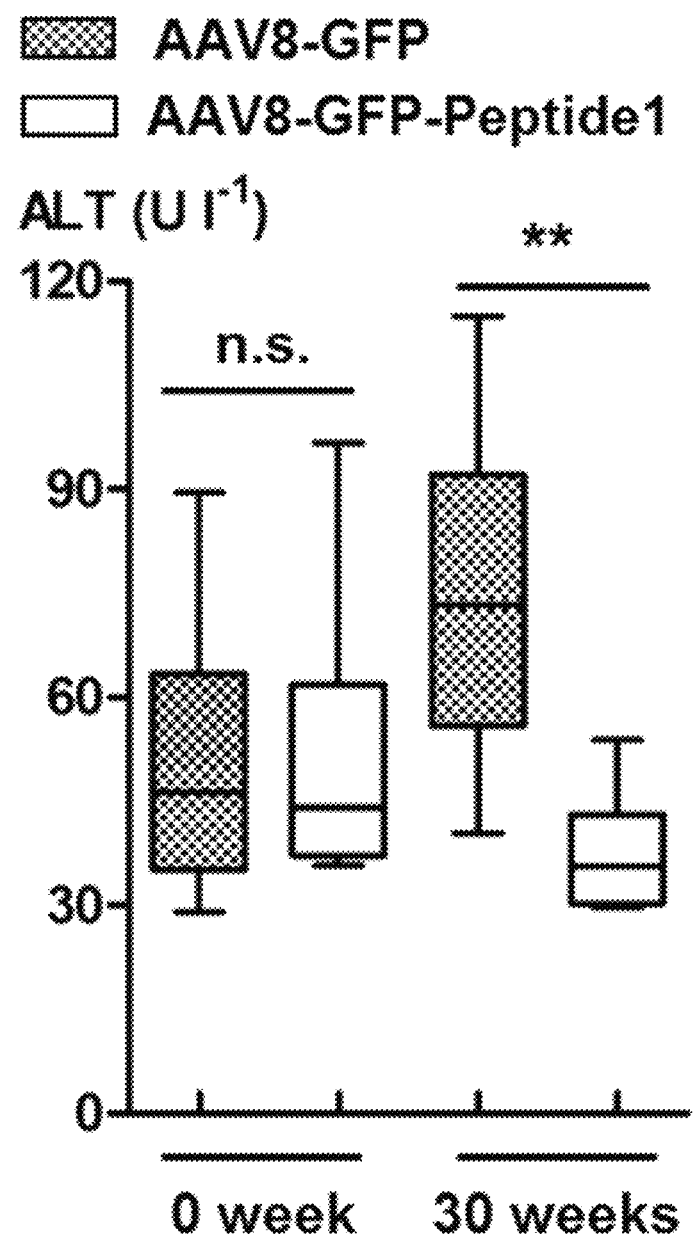
Figure 7F:
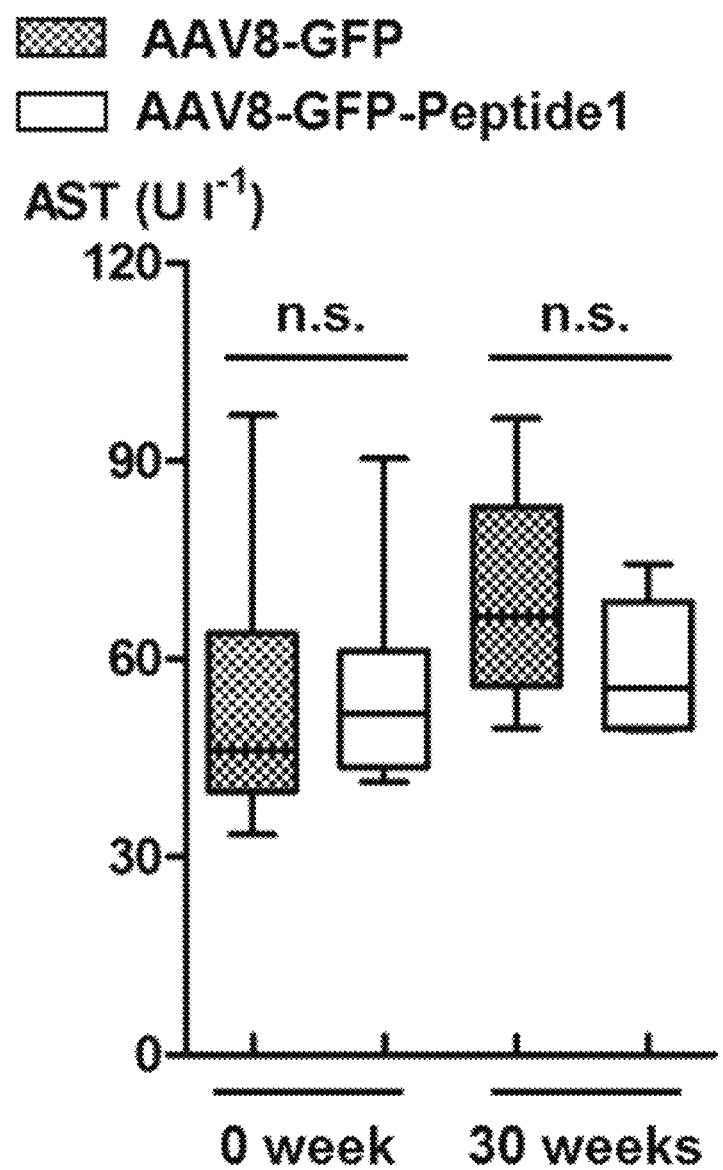

The detection results of blood lipids, ASL and AST are shown as FIGS. 7A-7F. After 30-week high-fat feeding, the level of serum triglyceride of the monkeys in AAV8-GFP-Peptide1 group is significantly lower than that of AAV8-GFP control group (FIG. 7A); there is no significant difference in serum total cholesterol between the two groups (FIG. 7B), while the level of serum high density cholesterol of AAV8-GFP-Peptide1 group is higher than that of AAV8-GFP group (FIG. 7C), and the level of low density cholesterol of AAV8-GFP-Peptide1 group is lower than that of AAV8-GFP group (FIG. 7D). There is no significant difference in AST level between the two groups, while the level of ALT of AAV8-GFP-Peptide1 group is significantly lower than that of AAV8-GFP group (FIG. 7E and FIG. 7F). These results indicate that Peptide1 peptide inhibits progression of liver dysfunction caused by high-fat diet and incidence of steatohepatitis.

Figure 8:
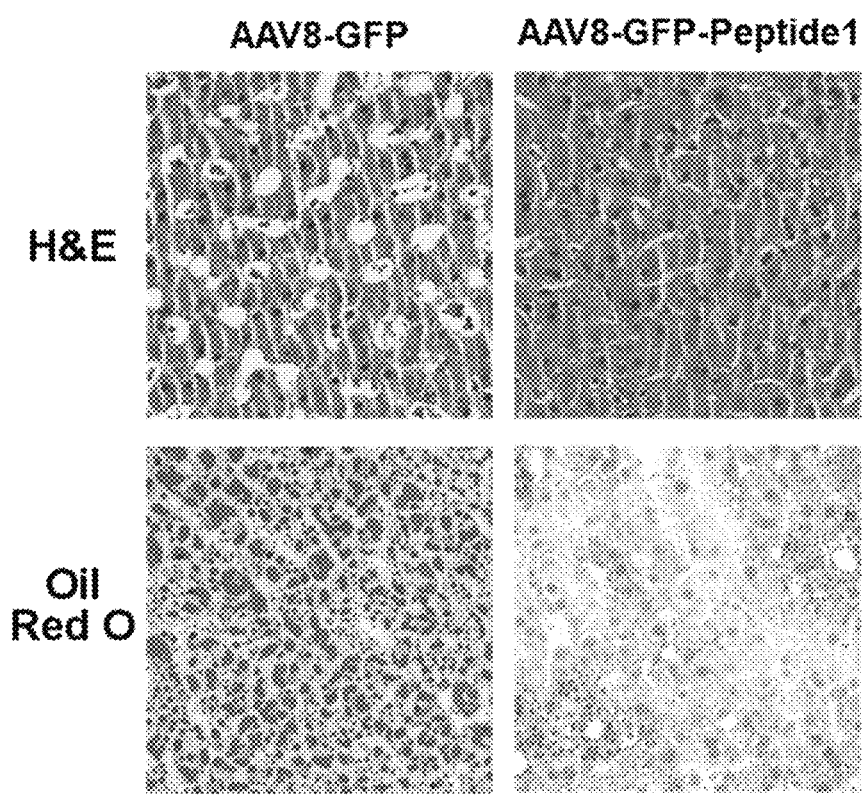
FIG. 8 illustrates a liver tissue HE and oil red O staining result of cynomolgus monkeys in AAV8-GFP and AAV8-GFP-Peptide1 group.

The pathological findings of liver tissues, as shown as FIG. 8, show that after 30 week high-fat feeding, the liver slices of monkeys of AAV8-GFP group appear obvious vacuolar and confluent and destructed liver cells under observation after HE staining, and vacuolization in AAV8-GFP-Peptide1 group is significantly reduced compared with that in AAV8-GFP group (FIG. 8). The results of oil red O staining show that a large red area is found around the hepatic portal vein of monkeys of AAV8-GFP group, indicating massive lipid accumulation, while in AAV8-GFP-Peptide1 group, the red area is significantly reduced, and the lipid accumulation is reduced (FIG. 8, lower portion). The pathological staining results show that over-expression of Peptide1 significantly reduces high-fat diet-induced liver steatosis and liver lipid accumulation in Cynomolgus monkeys. Peptide1 can inhibit the incidence of steatohepatitis in Cynomolgus monkeys.

The above results indicate that over-expression of Peptide1 can significantly alleviate HFD-induced steatohepatitis. Peptide1 has obvious effect on improving steatohepatitis. Peptide1 shows potential as a novel drug against steatohepatitis.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method of measuring a peptide's inhibition effect on N-terminal dimerization of apoptosis signal-regulated kinase 1, the method comprising:
   (a) contacting a system containing an N-terminal of the apoptosis signal-regulated kinase 1 with a candidate peptide, comprising:
      (1) constructing a cell model containing the N-terminal of the apoptosis signal-regulated kinase 1 using a mammalian two-hybrid system, comprising: connecting a DNA fragment encoding the N-terminal amino acids from 1 to 678 aa of the apoptosis signal-regulated kinase 1 to a pBIND vector encoding the DNA binding domain and to a pACT vector encoding transcriptional activation domain respectively to obtain two constructed vectors; transfecting the two constructed vectors into an animal cell to obtain a constructed animal cell model; wherein the N-terminal amino acids from 1 to 678 aa of the apoptosis signal-regulated kinase 1 are SEQ ID NO: 1 and a nucleotide sequence encoding the N-terminal amino acids from 1 to 678 aa of the apoptosis signal-regulated kinase 1 is SEQ ID NO: 2; and
      (2) connecting a DNA sequence encoding the candidate peptide to a psi-Flag vector to obtain a constructed candidate peptide plasmid, and simultaneously transfecting the constructed candidate peptide plasmid and pG5luc plasmid into the constructed animal cell model to obtain a transfected cell for screening the N-terminal dimerization of the apoptosis signal-regulated kinase 1; and
   (b) measuring inhibition effect of the candidate peptide on the N-terminal dimerization of the apoptosis signal-regulated kinase 1, comprising: measuring RLU of firefly luciferase and RLU of *Renilla* luciferase of the transfected cell after incubated for 24 h; calculating a ratio of the RLU of firefly luciferase to the RLU of *Renilla* luciferase as a degree of the inhibition effect of the candidate peptide on the N-terminal dimerization of apoptosis signal-regulated kinase 1; wherein when the N terminal of the apoptosis signal-regulated kinase 1 is normally dimerized, the firefly luciferase reporter gene is expressed in the transfected cells; and when the N terminal dimerization of the apoptosis signal-regulated kinase 1 is inhibited, the firefly luciferase reporter gene on the pG5luc vector is not expressed.

2. The method of claim 1, wherein the animal cell in (a) is HEK-293T, L02, Hela, Huh7, Hepg2, A549, 3T3, MEFs, and H9C2.

3. The method of claim 2, wherein the animal cell used in (a) is HEK-293T.

4. A method of measuring a peptide's inhibition effect on N-terminal dimerization of apoptosis signal-regulated kinase 1, the method comprising:
- (a) contacting a system containing an N-terminal of the apoptosis signal-regulated kinase 1 with a candidate peptide, comprising:
  - (1) constructing a cell model containing the N-terminal of the apoptosis signal-regulated kinase 1 using a mammalian two-hybrid system, comprising: connecting a DNA encoding the N-terminal amino acids from 1 to 678 aa of the apoptosis signal-regulated kinase 1 to plasmids pcDNA5-HA and pcDNA5-Myc, respectively, to obtain constructed plasmids HA-ASK1N and Myc-ASK1N; transfecting the constructed plasmids into an animal cell to obtain a constructed cell model; and
  - (2) connecting a DNA sequence encoding the candidate peptide to a psi-Flag vector to obtain a constructed peptide plasmid; and transfecting the constructed peptide plasmid into the constructed cell model; and
- (b) measuring inhibition effect of the candidate peptide on the N-terminal dimerization of the apoptosis signal-regulated kinase 1, comprising: detecting contents of HA-ASK1$_N$ and Myc-ASK1$_N$ in a protein solution after co-immunoprecipitation by Western blot after 24 hrs of incubation of the transfected cell; wherein co-immunoprecipitation is performed by using anti-HA to connect the target protein with protein A/G agarose beads, and Western blot is treated with anti-Myc as primary antibody; when the contents of HA-ASK1$_N$ and Myc-ASK1$_N$ of the transfected cell transfected with the constructed peptide plasmid, HA-ASK1$_N$, and Myc-ASK1$_N$ are identical to contents of HA-ASK1$_N$ and Myc-ASK1$_N$ of a control group transfected with HA-ASK1$_N$ or Myc-ASK1$_N$ alone, and no significant Myc protein band is detected, the candidate peptide is a potential substance for prevention, alleviation and/or treatment of steatohepatitis.

5. The method of claim 4, wherein the animal cell used in (a) is HEK-293T, L02, Hela, Huh7, Hepg2, A549, 3T3, MEFs, and H9C2.

6. The method of claim 5, wherein the animal cell used in (a) is HEK-293T.

7. The method of claim 6, further comprising performing a cellular experiments and/or animal tests to test the candidate peptide for prevention, alleviation and/or treatment of steatohepatitis.

* * * * *

SEQUENCE LISTING

```
<160> NUMBER OF SEQ ID NOS: 38

<210> SEQ ID NO 1
<211> LENGTH: 678
<212> TYPE: PRT
<213> ORGANISM: Artificial Sequence
<220> FEATURE:
<223> OTHER INFORMATION: Fully synthetic

<400> SEQUENCE: 1

Met Ser Thr Glu Ala Asp Glu Gly Ile Thr Phe Ser Val Pro Pro Phe
1               5                   10                  15

Ala Pro Ser Gly Phe Cys Thr Ile Pro Glu Gly Gly Ile Cys Arg Arg
            20                  25                  30
```

```
Gly Gly Ala Ala Val Gly Glu Gly Glu His Gln Leu Pro Pro
         35              40              45

Pro Pro Pro Gly Ser Phe Trp Asn Val Glu Ser Ala Ala Pro Gly
    50              55              60

Ile Gly Cys Pro Ala Ala Thr Ser Ser Ser Ala Thr Arg Gly Arg
65              70              75              80

Gly Ser Ser Val Gly Gly Ser Arg Arg Thr Thr Val Ala Tyr Val
             85              90              95

Ile Asn Glu Ala Ser Gln Gly Gln Leu Val Val Ala Glu Ser Glu Ala
             100             105             110

Leu Gln Ser Leu Arg Glu Ala Cys Glu Thr Val Gly Ala Thr Leu Glu
             115             120             125

Thr Leu His Phe Gly Lys Leu Asp Phe Gly Glu Thr Thr Val Leu Asp
             130             135             140

Arg Phe Tyr Asn Ala Asp Ile Ala Val Val Glu Met Ser Asp Ala Phe
145             150             155             160

Arg Gln Pro Ser Leu Phe Tyr His Leu Gly Val Arg Glu Ser Phe Ser
             165             170             175

Met Ala Asn Asn Ile Ile Leu Tyr Cys Asp Thr Asn Ser Asp Ser Leu
             180             185             190

Gln Ser Leu Lys Glu Ile Ile Cys Gln Lys Asn Thr Met Cys Thr Gly
             195             200             205

Asn Tyr Thr Phe Val Pro Tyr Met Ile Thr Pro His Asn Lys Val Tyr
             210             215             220

Cys Cys Asp Ser Ser Phe Met Lys Gly Leu Thr Glu Leu Met Gln Pro
225             230             235             240

Asn Phe Glu Leu Leu Leu Gly Pro Ile Cys Leu Pro Leu Val Asp Arg
             245             250             255

Phe Ile Gln Leu Leu Lys Val Ala Gln Ala Ser Ser Ser Gln Tyr Phe
             260             265             270

Arg Glu Ser Ile Leu Asn Asp Ile Arg Lys Ala Arg Asn Leu Tyr Thr
             275             280             285

Gly Lys Glu Leu Ala Ala Glu Leu Ala Arg Ile Arg Gln Arg Val Asp
             290             295             300

Asn Ile Glu Val Leu Thr Ala Asp Ile Val Asn Leu Leu Ser
305             310             315             320

Tyr Arg Asp Ile Gln Asp Tyr Asp Ser Ile Val Lys Leu Val Glu Thr
             325             330             335

Leu Glu Lys Leu Pro Thr Phe Asp Leu Ala Ser His His Val Lys
             340             345             350

Phe His Tyr Ala Phe Ala Leu Asn Arg Arg Asn Leu Pro Gly Asp Arg
             355             360             365

Ala Lys Ala Leu Asp Ile Met Ile Pro Met Val Gln Ser Glu Gly Gln
             370             375             380

Val Ala Ser Asp Met Tyr Cys Leu Val Gly Arg Ile Tyr Lys Asp Met
385             390             395             400

Phe Leu Asp Ser Asn Phe Thr Asp Thr Glu Ser Arg Asp His Gly Ala
             405             410             415

Ser Trp Phe Lys Lys Ala Phe Glu Ser Glu Pro Thr Leu Gln Ser Gly
             420             425             430

Ile Asn Tyr Ala Val Leu Leu Leu Ala Ala Gly His Gln Phe Glu Ser
             435             440             445
```

```
Ser Phe Glu Leu Arg Lys Val Gly Val Lys Leu Ser Leu Leu Gly
    450                 455                 460

Lys Lys Gly Asn Leu Glu Lys Leu Gln Ser Tyr Trp Glu Val Gly Phe
465                 470                 475                 480

Phe Leu Gly Ala Ser Val Leu Ala Asn Asp His Met Arg Val Ile Gln
                485                 490                 495

Ala Ser Glu Lys Leu Phe Lys Leu Lys Thr Pro Ala Trp Tyr Leu Lys
                500                 505                 510

Ser Ile Val Glu Thr Ile Leu Ile Tyr Lys His Phe Val Lys Leu Thr
                515                 520                 525

Thr Glu Gln Pro Val Ala Lys Gln Glu Leu Val Asp Phe Trp Met Asp
530                 535                 540

Phe Leu Val Glu Ala Thr Lys Thr Asp Val Thr Val Arg Phe Pro
545                 550                 555                 560

Val Leu Ile Leu Glu Pro Thr Lys Ile Tyr Gln Pro Ser Tyr Leu Ser
                565                 570                 575

Ile Asn Asn Glu Val Glu Glu Lys Thr Ile Ser Ile Trp His Val Leu
                580                 585                 590

Pro Asp Asp Lys Lys Gly Ile His Glu Trp Asn Phe Ser Ala Ser Ser
                595                 600                 605

Val Arg Gly Val Ser Ile Ser Lys Phe Glu Glu Arg Cys Cys Phe Leu
                610                 615                 620

Tyr Val Leu His Asn Ser Asp Asp Phe Gln Ile Tyr Phe Cys Thr Glu
625                 630                 635                 640

Leu His Cys Lys Lys Phe Phe Glu Met Val Asn Thr Ile Thr Glu Glu
                645                 650                 655

Lys Gly Arg Ser Thr Glu Glu Gly Asp Cys Glu Ser Asp Leu Leu Glu
                660                 665                 670

Tyr Asp Tyr Glu Tyr Asp
        675

<210> SEQ ID NO 2
<211> LENGTH: 2034
<212> TYPE: DNA
<213> ORGANISM: Artificial Sequence
<220> FEATURE:
<223> OTHER INFORMATION: Fully synthetic

<400> SEQUENCE: 2
atgagcacgg aggcggacga gggcatcact ttctctgtgc cacccttcgc ccctcgggc        60 ttctgcacca tccccgaggg cggcatctgc aggaggggag gagcggcggc ggtgggcgag      120
ggcgaggagc accagctgcc accgccgccg ccgggcagct tctggaacgt ggagagcgcc      180 gctgccctg gcatcggttg tccggcggcc acctcctcga gcagtgccac ccgaggccgg       240
ggcagctctg ttggcggggg cagccgacgg accacggtgg catatgtgat caacgaagcg      300
agccaagggc aactggtggt ggccgagagc gaggccctgc agagcttgcg ggaggcgtgc      360
gagacagtgg gcgccaccct ggaaaccctg catttttggga aactcgactt tggagaaacc     420
accgtgctgg accgctttta caatgcagat attgcggtgg tggagatgag cgatgccttc      480
cggcagccgt ccttgttta ccaccttggg gtgagagaaa gtttcagcat ggccaacaac      540
atcatcctct actgtgatac taactcggac tctctgcagt cactgaagga ataatttgc      600 cagaagaata ctatgtgcac tgggaactac acctttgttc cttacatgat aactccacat      660
aacaaagtct actgctgtga cagcagcttc atgaaggggt tgacagagct catgcaaccg      720
```

```
aacttcgagc tgcttcttgg acccatctgc ttacctcttg tggatcgttt tattcaactt    780
ttgaaggtgg cacaagcaag ttctagccag tacttccggg aatctatact caatgacatc    840
aggaaagctc gtaatttata cactggtaaa gaattggcag ctgagttggc aagaattcgg    900
cagcgagtag ataatatcga agtcttgaca gcagatattg tcataaatct gttactttcc    960
tacagagata tccaggacta tgattctatt gtgaagctgg tagagacttt agaaaaactg   1020
ccaacctttg atttggcctc ccatcaccat gtgaagtttc attatgcatt tgcactgaat   1080
aggagaaatc tccctggtga cagagcaaaa gctcttgata ttatgattcc catggtgcaa   1140
agcgaaggac aagttgcttc agatatgtat tgcctagttg gtcgaatcta caaagatatg   1200
tttttggact ctaatttcac ggacactgaa agcagagacc atggagcttc ttggttcaaa   1260
aaggcatttg aatctgagcc aacactacag tcaggaatta attatgcggt cctcctcctg   1320
gcagctggac accagtttga atcttccttt gagctccgga aagttggggt gaagctaagt   1380
agtcttcttg gtaaaaaggg aaacttggaa aaactccaga gctactggga agttggatt    1440 tttctggggg ccagcgtcct agccaatgac cacatgagag tcattcaagc atctgaaaag   1500 cttttttaaac tgaagacacc agcatggtac ctcaagtcta ttgtagagac aattttaata   1560
tataagcatt ttgtgaaact gaccacagaa cagcctgtgg ccaagcaaga acttgtggac   1620
ttttggatgg atttcctggt cgaggccaca aagacagatg ttactgtggt taggtttcca   1680
gtattaatat tagaaccaac caaaatctat caaccttctt atttgtctat caacaatgaa   1740
gttgaggaaa agacaatctc tatttggcac gtgcttcctg atgacaagaa aggtatacat   1800
gagtggaatt ttagtgcctc ttctgtcagg ggagtgagta tttctaaatt tgaagaaaga   1860
tgctgctttc tttatgtgct tcacaattct gatgatttcc aaatctattt ctgtacagaa   1920
cttcattgta aaaagttttt tgagatggtg aacaccatta ccgaagagaa ggggagaagc   1980
acagaggaag gagactgtga aagtgacttg ctggagtatg actatgaata tgat         2034

<210> SEQ ID NO 3
<211> LENGTH: 30
<212> TYPE: DNA
<213> ORGANISM: Artificial Sequence
<220> FEATURE:
<223> OTHER INFORMATION: Fully synthetic

<400> SEQUENCE: 3
cgggatccgg atgagcacgg aggcggacga                                       30

<210> SEQ ID NO 4
<211> LENGTH: 30
<212> TYPE: DNA
<213> ORGANISM: Artificial Sequence
<220> FEATURE:
<223> OTHER INFORMATION: Fully synthetic

<400> SEQUENCE: 4
tgatgtcatt ctggtgctcc tcgccctcgc                                       30

<210> SEQ ID NO 5
<211> LENGTH: 30
<212> TYPE: DNA
<213> ORGANISM: Artificial Sequence
<220> FEATURE:
<223> OTHER INFORMATION: Fully synthetic

<400> SEQUENCE: 5
ggagcaccag aatgacatca ggaaagctcg                                       30
```

<210> SEQ ID NO 6
<211> LENGTH: 36
<212> TYPE: DNA
<213> ORGANISM: Artificial Sequence
<220> FEATURE:
<223> OTHER INFORMATION: Fully synthetic

<400> SEQUENCE: 6
gctctagatc aatcatattc atagtcatac tccagc                          36

<210> SEQ ID NO 7
<211> LENGTH: 34
<212> TYPE: DNA
<213> ORGANISM: Artificial Sequence
<220> FEATURE:
<223> OTHER INFORMATION: Fully synthetic

<400> SEQUENCE: 7
gctctagagc caccatgctc cataatggga gaag                            34

<210> SEQ ID NO 8
<211> LENGTH: 37
<212> TYPE: DNA
<213> ORGANISM: Artificial Sequence
<220> FEATURE:
<223> OTHER INFORMATION: Fully synthetic

<400> SEQUENCE: 8
cgggatccct tgtcatcgtc gtccttgtaa tcaatgc                         37

<210> SEQ ID NO 9
<211> LENGTH: 51
<212> TYPE: DNA
<213> ORGANISM: Artificial Sequence
<220> FEATURE:
<223> OTHER INFORMATION: Fully synthetic

<400> SEQUENCE: 9
agcttgccac catgtaccca tacgatgttc cagattacgc tagcccgggc g          51

<210> SEQ ID NO 10
<211> LENGTH: 51
<212> TYPE: DNA
<213> ORGANISM: Artificial Sequence
<220> FEATURE:
<223> OTHER INFORMATION: Fully synthetic

<400> SEQUENCE: 10
gatccgcccg ggctagcgta atctggaaca tcgtatgggt acatggtggc a          51

<210> SEQ ID NO 11
<211> LENGTH: 29
<212> TYPE: DNA
<213> ORGANISM: Artificial Sequence
<220> FEATURE:
<223> OTHER INFORMATION: Fully synthetic

<400> SEQUENCE: 11
cgcggatcca ctagtccagt gtggtggaa                                  29

<210> SEQ ID NO 12
<211> LENGTH: 32
<212> TYPE: DNA
<213> ORGANISM: Artificial Sequence
<220> FEATURE:

<223> OTHER INFORMATION: Fully synthetic

<400> SEQUENCE: 12
cccaagctta agtttaaacg ctagagtccg ga          32

<210> SEQ ID NO 13
<211> LENGTH: 54
<212> TYPE: DNA
<213> ORGANISM: Artificial Sequence
<220> FEATURE:
<223> OTHER INFORMATION: Fully synthetic

<400> SEQUENCE: 13
agcttgccac catggagcag aagctgatct cagaggagga cctgagcccg ggcg          54

<210> SEQ ID NO 14
<211> LENGTH: 54
<212> TYPE: DNA
<213> ORGANISM: Artificial Sequence
<220> FEATURE:
<223> OTHER INFORMATION: Fully synthetic

<400> SEQUENCE: 14
gatccgcccg ggctcaggtc ctcctctgag atcagcttct gctccatggt ggca          54

<210> SEQ ID NO 15
<211> LENGTH: 293
<212> TYPE: DNA
<213> ORGANISM: Artificial Sequence
<220> FEATURE:
<223> OTHER INFORMATION: Fully synthetic

<400> SEQUENCE: 15
ccggctagcg attacgccaa gctcgaaatt aaccctcact aaagggaaca aaagctggag          60
ctccaccgcg gtggcggccg ccaccatgga ttacaaggat gacgacgata agagcccggg         120
cggatctatg gattacaagg atgacgacga taagagcccg gcggatcta tggattacaa         180 ggatgacgac gataagagcc cgggcggatc tatggattac aaggatgacg acgataagag         240
cccgggcgga tccgcgatac cggaattccg gaatccgctc gagcaattga tgc              293

<210> SEQ ID NO 16
<211> LENGTH: 28
<212> TYPE: DNA
<213> ORGANISM: Artificial Sequence
<220> FEATURE:
<223> OTHER INFORMATION: Fully synthetic

<400> SEQUENCE: 16
cgggatccat gagcacggag gcggacga          28

<210> SEQ ID NO 17
<211> LENGTH: 37
<212> TYPE: DNA
<213> ORGANISM: Artificial Sequence
<220> FEATURE:
<223> OTHER INFORMATION: Fully synthetic

<400> SEQUENCE: 17
tgcggccgct caatcatatt catagtcata ctccagc          37

<210> SEQ ID NO 18
<211> LENGTH: 28
<212> TYPE: DNA
<213> ORGANISM: Artificial Sequence
<220> FEATURE:
<223> OTHER INFORMATION: Fully synthetic

<400> SEQUENCE: 18
gaagatctat gagcacggag gcggacga                               28

<210> SEQ ID NO 19
<211> LENGTH: 38
<212> TYPE: DNA
<213> ORGANISM: Artificial Sequence
<220> FEATURE:
<223> OTHER INFORMATION: Fully synthetic

<400> SEQUENCE: 19
catgccatgg tcaatcatat tcatagtcat actccagc                    38

<210> SEQ ID NO 20
<211> LENGTH: 58
<212> TYPE: PRT
<213> ORGANISM: Artificial Sequence
<220> FEATURE:
<223> OTHER INFORMATION: Fully synthetic

<400> SEQUENCE: 20

Leu His Asn Gly Arg Ser Lys Glu Gln Arg Leu Lys Glu Gln Leu Gly
 1               5                  10                  15

Ala Gln Gln Glu Pro Val Lys Lys Ser Ile Gln Glu Ser Glu Ala Phe
            20                  25                  30

Leu Pro Gln Ser Ile Pro Glu Glu Arg Tyr Lys Met Lys Ser Lys Pro
        35                  40                  45

Leu Gly Ile Cys Leu Ile Ile Asp Cys Ile
    50                  55

<210> SEQ ID NO 21
<211> LENGTH: 58
<212> TYPE: PRT
<213> ORGANISM: Artificial Sequence
<220> FEATURE:
<223> OTHER INFORMATION: Fully synthetic

<400> SEQUENCE: 21

Met Ser Ala Glu Val Ile His Gln Val Glu Glu Ala Leu Asp Thr Asp
 1               5                  10                  15

Glu Lys Glu Met Leu Leu Phe Leu Cys Arg Asp Val Ala Ile Asp Val
            20                  25                  30

Val Pro Pro Asn Val Arg Asp Leu Leu Asp Ile Leu Arg Glu Arg Gly
        35                  40                  45

Lys Leu Ser Val Gly Asp Leu Ala Glu Leu
    50                  55

<210> SEQ ID NO 22
<211> LENGTH: 58
<212> TYPE: PRT
<213> ORGANISM: Artificial Sequence
<220> FEATURE:
<223> OTHER INFORMATION: Fully synthetic

<400> SEQUENCE: 22

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

```
Glu Gly Glu Gly Asp Ala Thr Tyr Gly Lys Leu Thr Leu Lys Phe Ile
        35                  40                  45

Cys Thr Thr Gly Lys Leu Pro Val Pro Trp
        50                  55

<210> SEQ ID NO 23
<211> LENGTH: 58
<212> TYPE: PRT
<213> ORGANISM: Artificial Sequence
<220> FEATURE:
<223> OTHER INFORMATION: Fully synthetic

<400> SEQUENCE: 23

Gly Val Gln Cys Phe Ser Arg Tyr Pro Asp His Met Lys Gln His Asp
1               5                   10                  15

Phe Phe Lys Ser Ala Met Pro Glu Gly Tyr Val Gln Glu Arg Thr Ile
            20                  25                  30

Phe Phe Lys Asp Asp Gly Asn Tyr Lys Thr Arg Ala Glu Val Lys Phe
        35                  40                  45

Glu Gly Asp Thr Leu Val Asn Arg Ile Glu
        50                  55

<210> SEQ ID NO 24
<211> LENGTH: 25
<212> TYPE: DNA
<213> ORGANISM: Artificial Sequence
<220> FEATURE:
<223> OTHER INFORMATION: Fully synthetic

<400> SEQUENCE: 24
cgggatccct ccataatggg agaag                                    25

<210> SEQ ID NO 25
<211> LENGTH: 24
<212> TYPE: DNA
<213> ORGANISM: Artificial Sequence
<220> FEATURE:
<223> OTHER INFORMATION: Fully synthetic

<400> SEQUENCE: 25
gctctagaaa tgcaatcgat tatc                                     24

<210> SEQ ID NO 26
<211> LENGTH: 23
<212> TYPE: DNA
<213> ORGANISM: Artificial Sequence
<220> FEATURE:
<223> OTHER INFORMATION: Fully synthetic

<400> SEQUENCE: 26
cgggatccat gtctgctgaa gtc                                      23

<210> SEQ ID NO 27
<211> LENGTH: 26
<212> TYPE: DNA
<213> ORGANISM: Artificial Sequence
<220> FEATURE:
<223> OTHER INFORMATION: Fully synthetic

<400> SEQUENCE: 27
gctctagatc acagttcagc caagtc                                   26

<210> SEQ ID NO 28
<211> LENGTH: 24
```

```
<212> TYPE: DNA
<213> ORGANISM: Artificial Sequence
<220> FEATURE:
<223> OTHER INFORMATION: Fully synthetic

<400> SEQUENCE: 28
cgggatccat ggtgagcaag ggcg                                           24

<210> SEQ ID NO 29
<211> LENGTH: 26
<212> TYPE: DNA
<213> ORGANISM: Artificial Sequence
<220> FEATURE:
<223> OTHER INFORMATION: Fully synthetic

<400> SEQUENCE: 29
gctctagatc accagggcac gggcag                                         26

<210> SEQ ID NO 30
<211> LENGTH: 23
<212> TYPE: DNA
<213> ORGANISM: Artificial Sequence
<220> FEATURE:
<223> OTHER INFORMATION: Fully synthetic

<400> SEQUENCE: 30
cgggatccgg cgtgcagtgc ttc                                            23

<210> SEQ ID NO 31
<211> LENGTH: 26
<212> TYPE: DNA
<213> ORGANISM: Artificial Sequence
<220> FEATURE:
<223> OTHER INFORMATION: Fully synthetic

<400> SEQUENCE: 31
gctctagatc actcgatgcg gttcac                                         26

<210> SEQ ID NO 32
<211> LENGTH: 47
<212> TYPE: DNA
<213> ORGANISM: Artificial Sequence
<220> FEATURE:
<223> OTHER INFORMATION: Fully synthetic

<400> SEQUENCE: 32
cccaagcttg gtaccactag tgtcgacgaa ttcggcagtg gagaggg                  47

<210> SEQ ID NO 33
<211> LENGTH: 33
<212> TYPE: DNA
<213> ORGANISM: Artificial Sequence
<220> FEATURE:
<223> OTHER INFORMATION: Fully synthetic

<400> SEQUENCE: 33
ggaagatctt tacttgtaca gctcgtccat gcc                                 33

<210> SEQ ID NO 34
<211> LENGTH: 54
<212> TYPE: DNA
<213> ORGANISM: Artificial Sequence
<220> FEATURE:
<223> OTHER INFORMATION: Fully synthetic

<400> SEQUENCE: 34
```

```
ctctagactc gagaccggtc ttaaggctag cgatatcgga tccaagcttg gtac        54

<210> SEQ ID NO 35
<211> LENGTH: 54
<212> TYPE: DNA
<213> ORGANISM: Artificial Sequence
<220> FEATURE:
<223> OTHER INFORMATION: Fully synthetic

<400> SEQUENCE: 35
caagcttgga tccgatatcg ctagccttaa gaccggtctc gagtctagag agct        54

<210> SEQ ID NO 36
<211> LENGTH: 23
<212> TYPE: DNA
<213> ORGANISM: Artificial Sequence
<220> FEATURE:
<223> OTHER INFORMATION: Fully synthetic

<400> SEQUENCE: 36
agcagcacga cttcttcaag tcc                                          23

<210> SEQ ID NO 37
<211> LENGTH: 23
<212> TYPE: DNA
<213> ORGANISM: Artificial Sequence
<220> FEATURE:
<223> OTHER INFORMATION: Fully synthetic

<400> SEQUENCE: 37
tgtagttgta ctccagcttg tgc                                          23

<210> SEQ ID NO 38
<211> LENGTH: 174
<212> TYPE: DNA
<213> ORGANISM: Artificial Sequence
<220> FEATURE:
<223> OTHER INFORMATION: Fully synthetic

<400> SEQUENCE: 38
ctccataatg ggagaagtaa agaacaaaga cttaaggaac agcttggcgc tcaacaagaa  60
ccagtgaaga aatccattca ggaatcagaa gcttttttgc ctcagagcat acctgaagag 120
agatacaaga tgaagagcaa gcccctagga atctgcctga taatcgattg catt        174
```